(12) United States Patent
Koeda et al.

(10) Patent No.: US 9,080,168 B2
(45) Date of Patent: Jul. 14, 2015

(54) TUBE AND PLUNGER DEVICE

(71) Applicant: Seiko Epson Corporation, Tokyo (JP)

(72) Inventors: Hiroshi Koeda, Suwa (JP); Fumio Takagi, Chino (JP)

(73) Assignee: Seiko Epson Corporation (JP)

( * ) Notice: Subject to any disclaimer, the term of this patent is extended or adjusted under 35 U.S.C. 154(b) by 105 days.

(21) Appl. No.: 13/909,208

(22) Filed: Jun. 4, 2013

(65) Prior Publication Data

US 2013/0330250 A1  Dec. 12, 2013

(30) Foreign Application Priority Data

Jun. 6, 2012  (JP) .................................. 2012-128664

(51) Int. Cl.
| | |
|---|---|
| *B01D 21/00* | (2006.01) |
| *B01L 3/00* | (2006.01) |
| *B01L 3/02* | (2006.01) |
| *B01L 3/14* | (2006.01) |
| *C12N 15/10* | (2006.01) |

(52) U.S. Cl.
CPC .............. *C12N 15/1013* (2013.01); *B01L 3/502* (2013.01); *B01L 2200/0631* (2013.01); *B01L 2200/0668* (2013.01); *B01L 2200/0673* (2013.01); *B01L 2300/047* (2013.01); *B01L 2300/0832* (2013.01); *B01L 2400/0478* (2013.01); *B01L 2400/065* (2013.01)

(58) Field of Classification Search
CPC combination set(s) only.
See application file for complete search history.

(56) References Cited

U.S. PATENT DOCUMENTS

2003/0073110 A1  4/2003  Aritomi et al.

FOREIGN PATENT DOCUMENTS

| JP | 2004-025148 | 1/2004 |
|---|---|---|
| JP | 2007-175002 | 7/2007 |
| JP | 2008-012490 | 1/2008 |
| JP | 2009-136250 | 6/2009 |
| JP | 2009-207459 | 9/2009 |

*Primary Examiner* — Jill Warden
*Assistant Examiner* — Julie Tavares
(74) *Attorney, Agent, or Firm* — Harness, Dickey & Pierce, P.L.C.

(57) ABSTRACT

A device includes: a tube having a first portion and a second portion; and a plunger insertable from the first portion side of the tube and having a tubular portion that can fit an inner surface of the first portion and a rod-like portion that can fit an inner surface of the second portion and is supported by the tubular portion, wherein when the tubular portion fits the inner surface of the first portion, a first state where the inner surface of the second portion and the rod-like portion are spaced apart from each other and a second state where the inner surface of the second portion and the rod-like portion fit together are formed, and in the first state, a communication path communicating the inside of the second portion with the inside of the tubular portion is formed, while in the second state, the communication path is blocked.

11 Claims, 14 Drawing Sheets

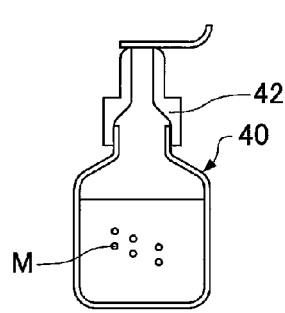
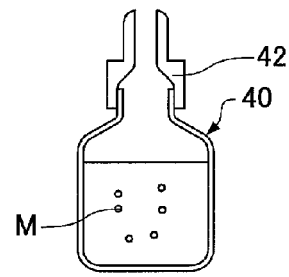
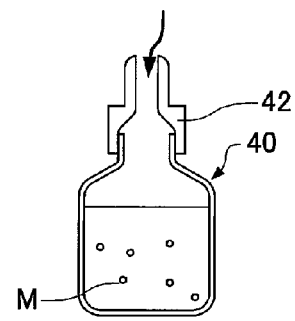
FIG.14A   FIG.14B   FIG.14C
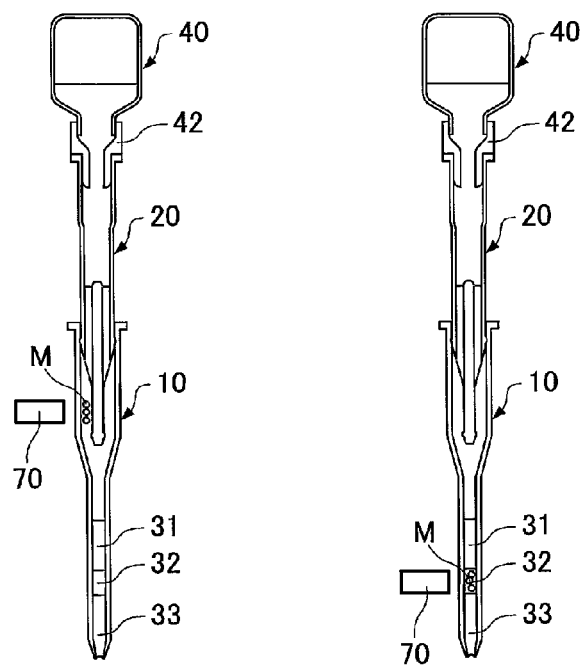
FIG.14D   FIG.14E

TUBE AND PLUNGER DEVICE

BACKGROUND

1. Technical Field

The present invention relates to a nucleic acid extracting or dispensing device.

2. Related Art

In the biochemical field, techniques of PCR (polymerase chain reaction) have been established. In recent years, amplification accuracy and detection sensitivity in the PCR method have been improved, and thus an extremely trace amount of specimen (such as DNA) can be amplified, detected, and analyzed. PCR is a method of applying thermal cycling to a solution (reaction solution) containing a nucleic acid as an amplification target (target nucleic acid) and a reagent to thereby amplify the target nucleic acid. As the thermal cycling of PCR, a method of applying thermal cycling at temperatures of two stages or three stages is usually adopted.

On the other hand, for the diagnosis of infectious diseases such as influenza at the site of medical care, the use of rapid test kits of immunochromatography and the like is the mainstream under the present circumstances. In such rapid tests, however, accuracy is sometimes insufficient, so that it is desired to apply PCR, from which higher test accuracy can be expected, to the diagnosis of infectious diseases. Moreover, in a general outpatient practice or the like in medical institutions, since the examination time is limited, the time that can be spent for a test is limited to a short time. Therefore, the reality is that a test for influenza, for example, is performed by a simple test such as immunochromatography, at the expense of test accuracy, for shortening the time.

Because of such circumstances, for realizing a test by PCR, from which higher accuracy can be expected, at the site of medical care, the time required for the reaction needs to be shortened. As an apparatus for performing PCR reaction in a short time, JP-A-2009-136250, for example, discloses a biological sample reaction apparatus that rotates a biological sample reaction chip filled with a reaction solution and a liquid that is not miscible with the reaction solution and has a specific gravity smaller than that of the reaction solution, about an axis of rotation in a horizontal direction to thereby move the reaction solution for applying thermal cycling. Moreover, as methods of PCR, a method of using magnetic beads (JP-A-2009-207459), a method of performing thermal cycling of PCR by moving a droplet in a temperature change region on a substrate using magnetic beads as moving means of the droplet (JP-A-2008-012490), and the like are disclosed.

Further, since specimens and reagents used for PCR are often rare and expensive, it is preferable that the amount (volume) of a reaction solution of PCR is smaller in view of cost and efficiency. Hence, a method that can handle the reaction solution of PCR in as small an amount as possible is desired. As an example of a method of handling a trace amount of liquid, JP-A-2004-025148 discloses a method of transferring a target liquid through a narrow tube using a sending liquid that is not miscible with the target liquid but is separable in phase therefrom. Moreover, JP-A-2007-175002 discloses, as a gene analyzing apparatus, an apparatus that performs PCR by moving a reaction solution of PCR within a channel, and a method of using the apparatus.

As described above, studies for shortening the time required for the thermal cycling of PCR are underway. However, the situation is that a technique for shortening the time required for extracting a nucleic acid serving as a template from a specimen to establish a state where PCR can be initiated has not been sufficiently developed. For example, for performing PCR, treatment (hereinafter sometimes simply referred to as "pretreatment") of extracting a nucleic acid (DNA (deoxyribonucleic acid) and/or RNA (ribonucleic acid)) serving as a template from a specimen (such as blood, nasal mucus, or oral mucosa) is needed. Even if the time required for the thermal cycling of PCR can be shortened, when the time required for extracting the nucleic acid (pretreatment) cannot be shortened, it is impossible to sufficiently meet demands at the site of medical care.

Although pretreatment using a column or magnetic beads is usually performed, all of the dispensing, stirring and centrifugal work, and the like of a reagent are manually performed, or an expensive and large-scale apparatus such as an automatic extraction apparatus is needed. Then, even in any of the methods, the time and effort for at least 30 minutes or more are required for the pretreatment. Hence, even if only the thermal cycling of PCR can be performed in a short time (for example, within 15 minutes), the reality is that at least about one hour is required for the overall test time from the collection of a specimen to a result of the test when the time required for the pretreatment is added.

Hence, it is realistically difficult, at the site with restrictions such as clinic hours, to consistently perform the test from the nucleic acid extraction (pretreatment) to the thermal cycling of PCR. Such a circumstance is one of obstacles for the widespread use of the test method using PCR in medical institutions. That is, the time and complication required for PCR itself and pretreatment are causes that make it difficult for the test method using PCR to come into widespread use at the site of medical care, in spite of the fact that PCR is a test method with higher sensitivity and higher accuracy than immunochromatography.

Moreover, in the method disclosed in the related art document, the volume of the target liquid to be handled is larger than $0.5\ \mu L$ (microliter). Therefore, the target liquid itself is prepared separately on a larger scale. Hence, preparation of the target liquid can be performed using, for example, instrument or an experimental tool available on the market. However, with improvement in microreaction techniques and increasing demand for cost reduction in PCR, preparation of the target liquid of a volume about $1\ \mu L$ is required. In such a case, an exact volume of solution containing a specimen and a reagent in orders of nanoliter (nL) (less than $1\ \mu L$) needs to be handled for measurement, sending, or the like. However, in the dispensing method in the related art, it is difficult to precisely handle a trace amount of liquid. For example, even when a manually operated pipette, which is perceived to be relatively precise, is used, it is difficult to measure, send, and dispense, with good accuracy, a liquid whose volume is as small as less than $0.2\ \mu L$.

SUMMARY

An advantage of some aspects of the invention is to provide a device that can shorten the time required for pretreatment for PCR. Another advantage of some aspects of the invention is to provide a device that can dispense a trace amount of liquid with good accuracy.

The invention can be implemented as the following aspects or application examples.

APPLICATION EXAMPLE 1

This application example of the invention is directed to a device including: a tube having a first portion and a second portion whose inside diameter is smaller than that of the first portion; and a plunger insertable from the first portion side of the tube and having a tubular portion that can fit an inner surface of the first portion and a rod-like portion that can fit an inner surface of the second portion and is supported by the tubular portion, wherein when the tubular portion fits the inner surface of the first portion, a first state where the inner surface of the second portion and the rod-like portion are spaced apart from each other and a second state where the inner surface of the second portion and the rod-like portion fit together are formed, and in the first state, a communication path communicating the inside of the second portion with the inside of the tubular portion is formed, while in the second state, the communication path is blocked.

In the device of the application example, a specimen or the like can be introduced, by bringing the device into the first state, into the second portion of the tube via the tubular portion. Then, by shifting the device from the first state to the second state, it is possible to constitute a syringe in the second portion of the tube. Therefore, a nucleic acid extraction operation of PCR, for example, can be performed with a very simple operation while suppressing contamination of the specimen or the like. Moreover, after bringing the device into the second state, the specimen or the like can be exactly discharged from the second portion of the tube, so that the specimen or the like can be exactly dispensed into another container or the like. Because of this, according to the device of the application example, pretreatment of PCR, for example, can be performed in simple and precise manners, and moreover, the time required for PCR can be shortened.

APPLICATION EXAMPLE 2

The device of Application Example 1 may be configured such that, in the inside of the second portion, a first plug including an oil, a second plug including an eluate not miscible with an oil, and a third plug including an oil are arranged in this order from the first portion side.

According to the device of the application example, the time and effort required for pretreatment for PCR can be considerably reduced. Specifically, an oil, an eluate, and an oil are arranged in order in the form of plugs in the second portion of the tube. Therefore, for example, when a specimen or the like is magnetic particles to which a target nucleic acid is adsorbed, the magnetic particles can be moved in the inside of the device, by applying a magnetic force from the outside of the device in the first state, to be introduced into the second portion of the tube via the tubular portion. Therefore, for example, the magnetic particles to which the nucleic acid is adsorbed can be introduced into the plunger, passed through the first plug, and moved to the second plug. Due to this, the nucleic acid extraction operation can be further exactly performed in a short time. Moreover, the magnetic particles can be moved as necessary, with the device remaining in the first state, from the second portion of the tube to another portion. Thereafter, when the device is brought into the second state and the plunger is moved in the tube, the third plug and the eluate can be discharged in this order from the second portion of the tube. Due to this, the effort to obtain an eluate containing nucleic acids at high purity can be considerably saved.

In the specification, the "plug" of a liquid indicates one in a form in which substantially only the liquid occupies the inside in a longitudinal direction of the tube, and indicates a state where a space in the inside of the tube is defined by the liquid. The term "substantially" as used herein indicates that a small amount of (for example, a thin film-like) another substance (a liquid or the like) may be present around the plug, that is, on the inner wall of the tube. Moreover, the "tube" indicates a tubular object having a cavity in the inside thereof. In the application example, the tube has an inner cavity, in which a liquid can maintain a plug in the tube, at least in the second portion.

Moreover, in the device of the application example, the eluate is sealed by the plugs of oil in the tube. Therefore, even when a tip of the tube on the second portion side is opened in the atmosphere or the like, evaporation of the eluate can be prevented. Due to this, for example, the volume of the eluate can be stabilized to be a predetermined size, so that the quantitation of the concentration of nucleic acid in the eluate can be maintained.

APPLICATION EXAMPLE 3

The device of Application Example 1 or 2 may be configured such that the device further includes a container connectable to the tubular portion, and when the container is connected to the tubular portion, the inside of the tubular portion and the inside of the container are communicated with each other.

In the device of the application example, when particles or the like and a specimen are accommodated in the container, nucleic acids can be adsorbed to the particles or the like in the container. Then, when the container is connected to the tubular portion, the particles or the like can be introduced into the tube. Moreover, since the device of the application example has the container, the container can be shaken independently, so that a liquid in the container can be sufficiently stirred. Due to this, the nucleic acids can be promptly adsorbed to the particles or the like.

Moreover, when the first to third plugs are arranged, the particles or the like to which the nucleic acids are adsorbed can be easily introduced, by connecting the container, from the first plug side of the tube and moved to the second plug. Due to this, nucleic acid extraction can be easily performed in a short time while suppressing contamination. More particularly, particles or the like to which nucleic acids are adsorbed are prepared in the container, the container is connected to the tubular portion of the plunger of the device in the first state, the particles or the like are introduced into the tube via the tubular portion and passed through the oil of the first plug, and the nucleic acids can be eluted from the particles or the like in the eluate of the second plug. Therefore, according to the device of the application example, the time and effort required for pretreatment for PCR can be considerably reduced.

APPLICATION EXAMPLE 4

The device of Application Example 1 or 2 may be configured such that the device has a plurality of the tubes and a plurality of the plungers, and the plurality of plungers and the plurality of tubes form, in conjunction with each other, the first state and the second state.

According to the device of the application example, arrangements of the plurality of tubes and the plurality of plungers can be simultaneously brought into the first state, and in that state, a specimen or the like can be introduced into the second portion of each of the tubes via the tubular portion of each of the plungers. Then, the arrangements of the plurality of tubes and the plurality of plungers can be simultaneously shifted from the first state to the second state. Due to this, it is possible to constitute a syringe in the second portion of each of the tubes. Therefore, pretreatment of PCR, for example, can be performed with a simple operation while suppressing contamination of the specimen or the like. Moreover, since the tubes and the plungers can be easily operated in conjunction with each other, the specimen or the like can be exactly discharged from the second portion of each of the tubes, so that the specimen or the like can be exactly dispensed into each of a plurality of containers or the like. Because of this, according to the device of the application example, pretreatment of PCR, for example, can be performed in more simple and precise manners, and moreover, the time required for PCR can be shortened.

APPLICATION EXAMPLE 5

The device of Application Example 4 may be configured such that the device further includes a manifold connectable to the tubular portions of the plurality of plungers, when the manifold is connected to the tubular portions, the insides of the tubular portions and the inside of the manifold are communicated with each other, and the manifold has a plurality of individual passages each connected to the tubular portion, and a common passage connected to the individual passages.

According to the device of the application example, since the device has the manifold, it is easy to evenly introduce particles or the like into the tubular portions of the plungers. Therefore, the time required for PCR, for example, can be further shortened.

APPLICATION EXAMPLE 6

The device of Application Example 5 may be configured such that the volumes of the individual passages are substantially equal to each other.

According to the device of the application example, substantially the same volume of liquid can be easily distributed and introduced into each of the tubular portions of the plungers with a simple operation. The phrase "substantially equal" as used herein means to include some differences due to dimension accuracy of a member or error in operation. That is, the "substantially equal volume" indicates that, for example, a difference in volume to be compared falls within a range of ±10% and preferably within a range of ±5%.

APPLICATION EXAMPLE 7

The device of Application Example 5 or 6 may be configured such that the device further includes a container connectable to the common passage of the manifold, and when the container is connected to the manifold, the inside of the manifold and the inside of the container are communicated with each other.

In the device of the application example, when particles or the like and a specimen are accommodated in the container, nucleic acids can be adsorbed to the particles or the like in the container. Then, when the container is connected to the manifold, the particles or the like can be introduced into the tubes. Moreover, since the device of the application example has the container, the container can be shaken independently, so that a liquid in the container can be sufficiently stirred. Due to this, the nucleic acids can be promptly adsorbed to the particles or the like.

Moreover, when the first to third plugs are arranged, the particles or the like to which the nucleic acids are adsorbed can be easily introduced, by connecting the container, from the first plug side of the tube and moved to the second plug. Due to this, the nucleic acid extraction can be performed in an extremely short time. More particularly, particles or the like to which nucleic acids are adsorbed are prepared in the container, the container is connected to the manifold of the device in the first state, the particles or the like are introduced into the tube via the tubular portion and passed through the oil of the first plug, and the nucleic acids can be eluted from the particles or the like in the eluate of the second plug. Then, the eluate can be dispensed into a plurality of other containers. Therefore, according to the device of the application example, the time and effort required for pretreatment for PCR can be considerably reduced.

BRIEF DESCRIPTION OF THE DRAWINGS

The invention will be described with reference to the accompanying drawings, wherein like numbers reference like elements.

FIGS. 14A to 14E schematically show steps of a nucleic acid extraction method using a device.

DESCRIPTION OF EXEMPLARY EMBODIMENTS

Hereinafter, some embodiments of the invention will be described. The embodiments described below describe examples of the invention. The invention is not limited to the embodiments below and includes various kinds of modified forms implemented within a range not changing the gist of the invention. Not all of configurations described below are indispensable constituent features of the invention.

1. Device

A device according to an embodiment of the invention includes a tube and a plunger.

Figure 1:
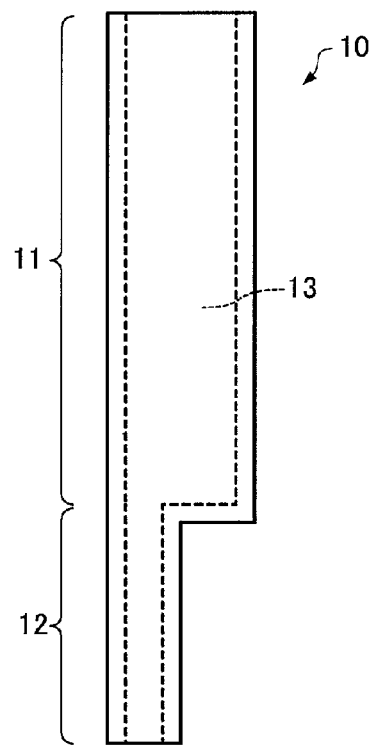
FIG. 1 schematically shows a tube of a device.
Figure 2:
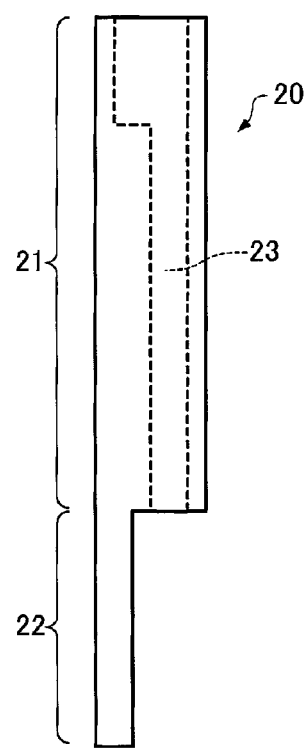
FIG. 2 schematically shows a plunger of the device.
Figure 3:
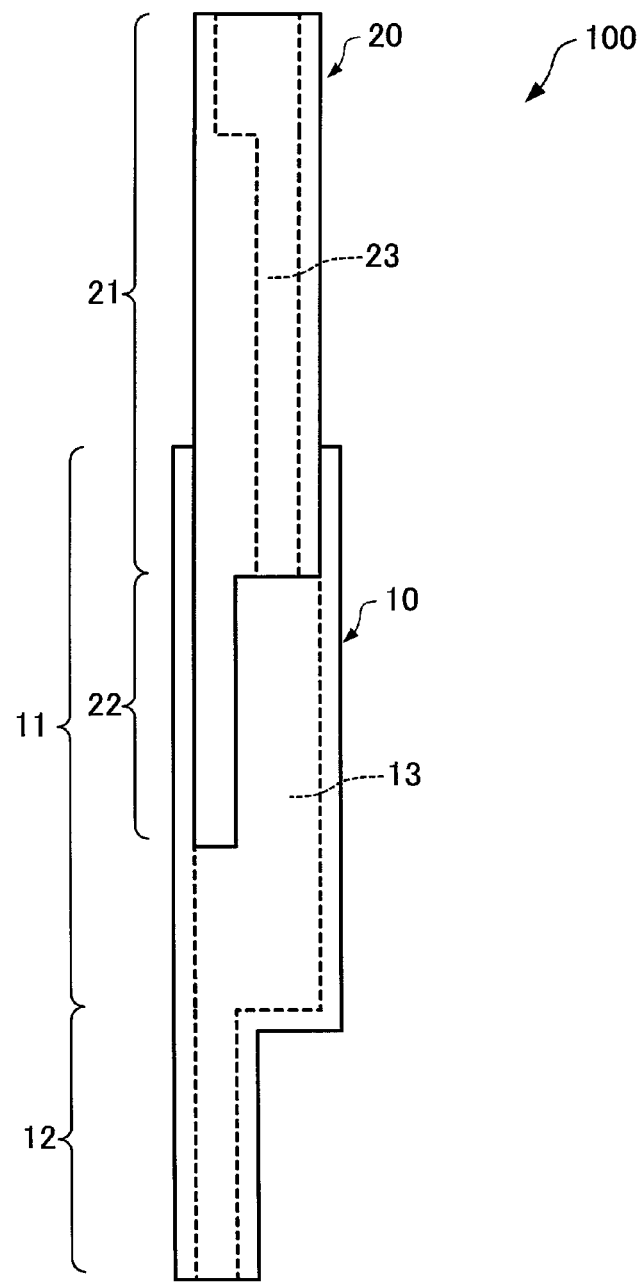
FIG. 3 schematically shows a first state of the device.
Figure 4:
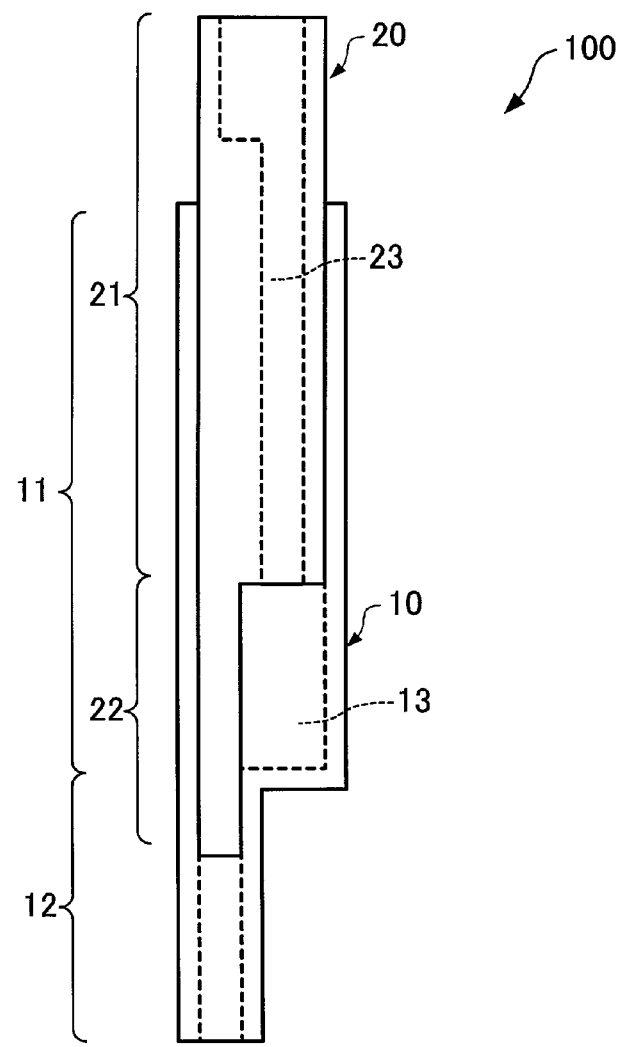
FIG. 4 schematically shows a second state of the device.

FIG. 1 conceptually shows a tube 10 of a device 100 of an embodiment. FIG. 2 conceptually shows a plunger 20 of the device 100 of the embodiment. FIGS. 3 and 4 schematically show the device 100 adopting a first state and a second state, respectively. All of FIGS. 1 to 4 are schematic views depicted in a simplified manner for describing the device according to the embodiment of the invention.

1.1. Tube

As shown in FIG. 1, the tube 10 has a tubular shape in which both ends are opened. The shape of the tube 10 is not particularly limited as long as the tube 10 has an inner cavity 13 penetrating therethrough and a first portion 11 and a second portion 12 described below. The inner cavity 13 of the tube 10 is a space through which, when a liquid is introduced, the liquid can flow in a longitudinal direction of the tube 10. The tube 10 has a shape that can cover a portion, a plurality of portions, or the whole of the plunger 20 when the plunger 20 is inserted. The tube 10 has a function as a cylinder. When the plunger 20 is inserted, the tube 10 can change, through sliding, the volume of the inner cavity 13 located closer to the tip side than a covering position with the plunger 20.

The tube 10 has the longitudinal direction but may bend. The shape of a cross-section of the inner cavity 13 of the tube 10, where the cross-section is perpendicular to the longitudinal direction, can be a circle, an ellipse, a polygon, or the like, and is not particularly limited. Moreover, the shape of a cross-section of the inner cavity 13 of the tube 10, where the cross-section is normal to the longitudinal direction, may be changed along the longitudinal direction of the tube 10. Whether or not a liquid can maintain a plug shape in the tube 10 when the liquid is introduced depends on conditions such as the material of the tube 10 or the kind of the liquid. Therefore, the shape of the cross-section of the tube 10, where the cross-section is normal to the longitudinal direction, is appropriately designed, as necessary, within a range in which the liquid can maintain a plug shape in the tube 10. Moreover, the tube 10 may bend or have flexibility as long as the tube 10 allows the plunger 20 to slide (slide in close contact therewith).

The shape of a cross-section of an external form of the tube 10, where the cross-section is normal to the longitudinal direction, is also not limited. Further, the wall thickness (length from a side surface to an outer surface of the inner cavity 13) of the tube 10 is also not particularly limited, and may be changed along the longitudinal direction of the tube 10. When a cross-section of the inner cavity 13 of the tube 10, where the cross-section is normal to the longitudinal direction, has a circular shape, the inside diameter (diameter of a circle in the cross-section of the inner cavity 13, where the cross-section is normal to the longitudinal direction) of the tube 10 can be set to, for example, from 0.5 mm to 5 mm. When the inside diameter of the tube 10 falls within this range, it is easy to form a plug of a liquid in a wide range in terms of, for example, the material of the tube 10 and the kind of the liquid, which is more preferable.

Although not particularly limited, the material of the tube 10 can be, for example, glass, a high polymer, a metal, or the like. However, when a material having transparency for visible light, such as glass or a high polymer, is selected for the material of the tube 10, the inside (the inner cavity 13) of the tube 10 can be observed from the outside thereof, which is more preferable. Moreover, when a substance transmitting a magnetic force, or a non-magnetic substance is selected for the material of the tube 10, introduction or the like of magnetic particles into the tube 10 is easily performed by giving a magnetic force from the outside of the tube 10, which is preferable.

The tube 10 has the first portion 11 and the second portion 12. The first portion 11 has an end at one of openings of the tube 10, and is a region extending in the longitudinal direction of the tube 10. The second portion 12 has an end at the other opening of the tube 10, and is a region extending in the longitudinal direction of the tube 10. The first portion 11 and the second portion 12 may be connected to each other, or may be spaced apart from each other.

The area of a cross-section of the inner cavity 13 in the first portion 11, where the cross-section is perpendicular to the longitudinal direction, is greater than that of a cross-section of the inner cavity 13 in the second portion 12, where the cross-section is perpendicular to the longitudinal direction. When the cross-section of the inner cavity 13, where the cross-section is perpendicular to the longitudinal direction, has a circular shape, the inside diameter of the tube 10 in the first portion 11 is greater than that of the tube 10 in the second portion 12.

The first portion 11 is a portion that fits a tubular portion 21 of the plunger 20 when the plunger 20 is inserted into the tube 10. That is, the tubular portion 21 of the plunger 20 fits an inner surface of the first portion 11 of the tube 10. Then, in the state where the tubular portion 21 of the plunger 20 fits the inner surface of the first portion 11 of the tube 10, the plunger 20 can be slid relative to the tube 10 while being in close contact therewith.

The first portion 11 of the tube 10 can have any length in the longitudinal direction as long as the length falls within a range in which the first state and the second state that will be described later can be formed and the plunger 20 can be slid in these states.

The second portion 12 is a portion that fits a rod-like portion 22 of the plunger 20 when the plunger 20 is inserted into the tube 10. That is, the rod-like portion 22 of the plunger 20 fits an inner surface of the second portion 12 of the tube 10. Then, in the state where the rod-like portion 22 of the plunger 20 fits the inner surface of the second portion 12 of the tube 10, the plunger 20 can be slid relative to the tube 10 while being in close contact therewith.

The second portion 12 of the tube 10 can have any length in the longitudinal direction as long as the length falls within a range in which the first state and the second state that will be described later can be formed and the plunger 20 can be slid in these states.

In the example of FIG. 1, the first portion 11 and the second portion 12 are contiguous, and the inside diameter of the inner cavity 13 is changed at a portion where the first portion 11 and the second portion 12 are connected. In the example of FIG. 1, the inner cavity 13 of the second portion 12 is connected, relative to the inner cavity 13 of the first portion 11, at a position shifted from the center. However, the arrangement is not limited. The inner cavity 13 of the second portion 12 may be connected, relative to the inner cavity 13 of the first portion 11, so as to have a common center. Moreover, in the example of FIG. 1, the inside diameter of the tube 10 is steeply changed at the connecting position of the first portion 11 and the second portion 12. However, the inside diameter may be smoothly changed. In this case, a portion where the inside diameter of the tube 10 is smoothly changed may be deemed as the first portion 11, or may be deemed as another portion formed between the first portion 11 and the second portion 12. Further, in the example of FIG. 1, the wall thickness of the tube 10 is depicted as substantially constant in the respective portions. However, for example, the wall thickness may be increased in the second portion 12 so that the external form of the first portion 11 and the second portion 12 is smoothly changed. For example, the external form of the tube 10 may be a cylindrical column shape in which the first portion 11 and the second portion 12 have the same diameter.

1.2. Plunger

As shown in FIG. 2, the plunger 20 has the tubular portion 21 and the rod-like portion 22. The plunger 20 has a rod-like shape in which the rod-like portion 22 is supported by the tubular portion 21. The plunger 20 can be inserted from the first portion 11 side of the tube 10 with the rod-like portion 22 as a tip. When inserted into the tube 10, at least a portion of the tubular portion 21 can internally contact the first portion 11 of the tube 10. Moreover, when inserted into the tube 10, the rod-like portion 22 can internally contact the second portion 12 of the tube 10. When inserted into the tube 10, the plunger 20 can slide in the tube 10.

The plunger 20 can function as a piston of a syringe. That is, it is possible, by sliding the plunger 20, to change the volume of the inner cavity 13 of the tube 10 located closer to the tip side of the plunger 20 than a position where the plunger 20 and the tube 10 contact each other. When the tube 10 and the plunger 20 adopt a second arrangement that will be described later, the position of the plunger 20 contacting the tube 10 is at the rod-like portion 22. Therefore, the rod-like portion 22 of the plunger 20 and the second portion 12 of the tube 10 constitute a syringe.

The tubular portion 21 and the rod-like portion 22 can internally contact the first portion 11 and the second portion 12, respectively, of the tube 10 described above. The tubular portion 21 and the rod-like portion 22 may entirely contact or partially contact the tube 10 as long as the plunger 20 has the function described above. Moreover, FIG. 2 shows an example in which the entire side surfaces of the tubular portion 21 and the rod-like portion 22 contact the inner surface of the tube 10. However, the tubular portion 21 and the rod-like portion 22 may contact the tube 10 via a gasket or an O-ring, or a convex portion may be formed in each of the tubular portion 21 and the rod-like portion 22 so that the tubular portion 21 and the rod-like portion 22 may contact the tube 10 via the convex portions.

The tubular portion 21 can fit the inner surface of the first portion 11 of the tube 10. The tubular portion 21 has an inner cavity 23 penetrating therethrough in the longitudinal direction. The inner cavity 23 is a space through which, when a liquid is introduced, the liquid can flow in the inside of the plunger 20 in the longitudinal direction. The inner cavity 23 of the tubular portion 21 penetrates from one end side to the other end side of the tubular portion 21, and serves as a space communicating the outside and inside of the device 100 with each other when a first arrangement that will be described later is adopted. More specifically, when the device 100 adopts the first arrangement, the inner cavity 23 of the tubular portion 21 can form a space communicating from the end of the plunger 20 on the tubular portion 21 side in the longitudinal direction to the side of the rod-like portion 22 of the plunger 20.

The rod-like portion 22 can fit the inner surface of the second portion 12 of the tube 10. When the device 100 is brought into the second state, the rod-like portion 22 can fit the inner surface of the second portion 12 of the tube 10 and slide in the longitudinal direction of the device 100. Due to this, the second portion 12 of the tube 10 and the rod-like portion 22 of the plunger 20 can constitute a syringe. In this case, the rod-like portion 22 of the plunger 20 is a piston, while the second portion 12 of the tube 10 is a cylinder.

The shape of a cross-section of the rod-like portion 22, where the cross-section is perpendicular to the longitudinal direction, can be a circle, an ellipse, a polygon, or the like, and is not particularly limited as long as the rod-like portion 22 can fit an inner wall of the second portion 12 of the tube 10.

The plunger 20 has the longitudinal direction but may bend along the tube 10. The material of the tubular portion 21 and the rod-like portion 22 of the plunger 20 is not particularly limited, and can be, for example, glass, a high polymer, a metal, or the like. Moreover, the tubular portion 21 and the rod-like portion 22 of the plunger 20 may be integrally formed of the same material or may be formed of different materials. Moreover, a form in which the rod-like portion 22 is supported by the tubular portion 21 is also not particularly limited. The rod-like portion 22 may be supported in a state of being formed integrally, may be formed separately to be coupled through another member, or may integrally or separately have a configuration such as a support member and be supported by the tubular portion 21 via the support member.

When, for example, the end of the tube 10 on the first portion 11 side is sealed by a film or the like, a form may be adopted in which, in inserting the plunger 20, the rod-like portion 22 of the plunger 20 breaks through the film and therefore is inserted.

1.3. Positional Relation Between Tube and Plunger

FIG. 3 is a schematic view showing an arrangement of the tube 10 and the plunger 20 when the device 100 is in the first state. FIG. 4 is a schematic view showing an arrangement of the tube 10 and the plunger 20 when the device 100 is in the second state.

As has been described above, the plunger 20 can be inserted into the tube 10, with the rod-like portion 22 as the tip, from the first portion 11 side of the tube 10. When the plunger 20 is inserted, the tubular portion 21 of the plunger 20 first fits the inner surface of the first portion 11 of the tube 10. In this state, the second portion 12 of the tube 10 and the rod-like portion 22 of the plunger 20 are spaced apart from each other (the first state). Then, when the plunger 20 is further inserted into the tube 10, the tubular portion 21 of the plunger 20 fits the inner surface of the first portion 11 of the tube 10 and a state where the rod-like portion 22 of the plunger 20 fits the inner surface of the second portion 12 of the tube 10 is formed (the second state). The device 100 according to the embodiment can adopt the first state illustrated in FIG. 3 and the second state illustrated in FIG. 4.

In the first state as illustrated in FIG. 3, when the tubular portion 21 of the plunger 20 fits the inner surface of the first portion 11 of the tube 10, the inner surface of the second portion 12 of the tube 10 and the rod-like portion 22 of the plunger 20 are spaced apart from each other. Moreover, in the second state as illustrated in FIG. 4, the tubular portion 21 of the plunger 20 fits the inner surface of the first portion 11 of the tube 10 and the inner surface of the second portion 12 of the tube 10 and the rod-like portion 22 of the plunger 20 fit together. In this manner, a communication path communicating the inside of the second portion 12 of the tube 10 with the inside of the tubular portion 21 of the plunger 20 is formed in the first state, while the communication path is blocked in the second state.

FIGS. 3 and 4 show examples of the first state and the second state, respectively. The state where the positional relation described above is established is not limited to the examples shown in FIGS. 3 and 4. Moreover, in the examples shown in FIGS. 3 and 4, the first portion 11 and the second portion 12 of the tube 10 and the tubular portion 21 and the rod-like portion 22 of the plunger 20 are illustrated as having the same lengths. However, these lengths can be appropriately changed as long as the first state and the second state can be formed.

In the device 100 according to the embodiment, when the first state is adopted, a space communicating from the outside world via the tubular portion 21 of the plunger 20 to the inside of the second portion 12 of the tube 10 can be formed. Moreover, in the device 100 according to the embodiment, when the second state is adopted, the rod-like portion 22 of the plunger 20 and the second portion 12 of the tube 10 can constitute a syringe.

1.4. Action and Effect

In the device 100 of the embodiment, a specimen or the like can be introduced, in the first state, from the outside of the device 100 via the tubular portion 21 of the plunger 20 into the second portion 12 of the tube 10. Then, by sliding the plunger 20 relative to the tube 10, the device 100 can be shifted from the first state to the second state. Due to this, it is possible to constitute a syringe in the second portion 12 of the tube 10. Therefore, a nucleic acid extraction operation or dispensing operation for PCR, for example, can be performed with a very simple operation while suppressing contamination of the specimen or the like introduced from the outside. Moreover, after the device 100 is brought into the second state, the specimen or the like can be exactly discharged from the second portion 12 of the tube 10, so that the specimen or the like can be exactly dispensed into another reaction container or the like. Hence, according to the device 100, pretreatment of PCR, for example, can be performed in simple and precise manners, and moreover, the time required for PCR can be shortened.

1.5. Other Configurations

The device according to the embodiment may include, in addition to the tube 10 and the plunger 20 described above, various configurations, such as a plug, a container, or a stopper, described below. Moreover, the configurations described below can be applied in combination with each other.

1.5.1. Plugs

Figure 5:
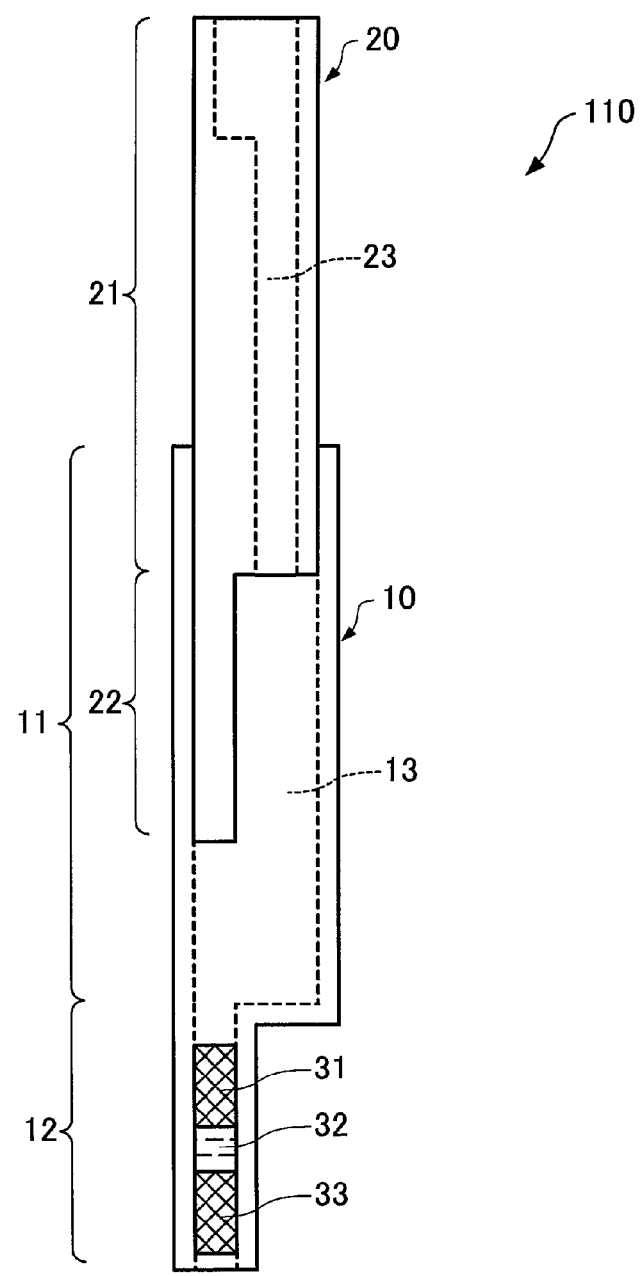
FIG. 5 schematically shows a device.

FIG. 5 schematically shows a device 110 in which plugs are arranged. In the device 110, in the inside of the second portion 12 of the tube 10, a first plug 31 including an oil, a second plug 32 including an eluate not miscible with an oil, and a third plug 33 including an oil not miscible with the eluate are arranged in this order from the first portion 11 side of the tube 10.

1.5.1.1. First Plug and Third Plug

Both of the first plug 31 and the third plug 33 include an oil. The oils of the first plug 31 and the third plug 33 may be different in kind from each other. Examples of oils include, for example, one kind selected from a silicone-based oil such as a dimethyl silicone oil, a paraffin-based oil, a mineral oil, and a mixture of them. Moreover, liquids for forming adjacent plugs among the first plug 31, the second plug 32, and the third plug 33 are selected such that the liquids are not miscible with each other.

The second plug 32 is arranged between the first plug 31 and the third plug 33. In a region of the first plug 31 on the side opposite to the second plug 32, another plug of liquid may be arranged, or another liquid introduced from the tubular portion 21 of the plunger 20 or the first portion 11 of the tube 10 may be arranged. Although it is preferable that there is no air bubble or another liquid in the first plug 31, an air bubble or another liquid may be present as long as particles or the like to which nucleic acids are adsorbed can pass through the first plug 31. Moreover, although it is preferable that there is no air bubble or another liquid between the first plug 31 and the second plug 32, an air bubble or another liquid may be present as long as particles or the like to which nucleic acids are adsorbed can pass from the first plug 31 to the second plug 32. Similarly, although it is preferable that there is no air bubble or another liquid between the second plug 32 and the third plug 33, an air bubble or another liquid may be present as long as particles or the like to which nucleic acids are adsorbed can pass from the second plug 32 to the third plug 33.

Also in a region of the third plug 33 on the side opposite to the second plug 32, another plug of liquid may be arranged. Although it is preferable that there is no air bubble or another liquid in the third plug 33, an air bubble or another liquid may be present.

The length of each of the first plug 31 and the third plug 33 in the longitudinal direction of the tube 10 is not particularly limited as long as the length falls within a range in which the plug can be formed. A specific length of the first plug 31 and the third plug 33 in the longitudinal direction of the tube 10 is from 1 mm to 50 mm, preferably from 1 mm to 30 mm so that the travel distance of particles or the like is not made too large, and further preferably from 5 mm to 20 mm. Among them, in the case where the length of the first plug 31 in the longitudinal direction of the tube 10 is lengthened, when the second plug 32 is discharged from the second portion 12 end of the tube 10, a liquid or the like arranged closer to the first portion 11 side of the tube 10 than the first plug 31 can be hardly discharged. In this case, a specific length of the first plug 31 can be from 10 mm to 50 mm.

Even when at least one end of the tube 10 is opened, the first plug 31 and the third plug 33 each have the function of preventing the substance exchange of an eluate (the second plug 32) with outside air, such as evaporation, or the contamination thereof from the outside. Therefore, even when at least one end of the tube 10 is opened in outside air, the volume of the eluate can be kept constant, and thus the concentration fluctuations or contamination of a liquid can be suppressed. Due to this, the concentration accuracy of nucleic acid or various medicines in nucleic acid extraction can be enhanced.

1.5.1.2. Second Plug

The second plug 32 is arranged at a position between the first plug 31 and the third plug 33 in the second portion 12 of the tube 10. The second plug 32 includes an eluate. The "eluate" indicates a liquid that desorbs nucleic acids adsorbed to particles or the like from the particles and elutes the nucleic acids into the liquid. Examples of eluates include, for example, purified water such as sterile water, distilled water, or ion-exchange water, and an aqueous solution obtained by dissolving, in such waters, at least one kind of an enzyme, a dNTP, a probe, a primer, and a buffer. The eluate is a liquid miscible with neither of the oil constituting the first plug 31 nor the oil constituting the third plug 33.

When the eluate is water or an aqueous solution, particles or the like to which nucleic acids are adsorbed are immersed in the eluate, whereby the nucleic acids adsorbed to the particles or the like can be released (eluted). Moreover, when an aqueous solution obtained by dissolving at least one kind of an enzyme, a dNTP, a probe, a primer, and a buffer is selected for the eluate, the nucleic acids adsorbed to the particles or the like are released (eluted) and a portion or the whole of components necessary for a reaction solution of PCR can be contained in the eluate. Therefore, the time and effort to prepare a reaction solution of PCR using an eluate can be further saved. The concentration of at least one kind of an enzyme, a dNTP, a probe, a primer, and a buffer to be dissolved for the eluate of the second plug 32 is not particularly limited, and can be set according to the reaction solution of PCR to be prepared.

Here, the dNTP represents four kinds of deoxyribonucleotide triphosphates (a mixture of dATP (deoxyadenosine triphosphate), dCTP (deoxycytidine triphosphate), dGTP (deoxyguanosine triphosphate), and dTTP (thymidine triphosphate)).

The volume of the second plug 32 is not particularly limited, and can be appropriately set using, as an index, the amount or the like of particles or the like to which nucleic acids are adsorbed. For example, when the volume of the particles or the like is 0.5 µL, it is sufficient that the volume of the second plug 32 is 0.5 µL or more, and the volume of the second plug 32 is preferably from 0.8 µL to 5 µL and further preferably from 1 µL to 3 µL. If the volume of the second plug 32 falls within this range, when the volume of the particles or the like is 0.5 µL, elution of the nucleic acids from the particles or the like can be sufficiently performed. For the elution of the nucleic acids from the particles or the like, the volume of the second plug 32 can be appropriately set with consideration that the heat capacity of a reaction solution is not made too large, in consideration of the length and diameter of the second portion 12 of the tube 10 and the promptness of thermal cycling of PCR.

1.5.1.3. Action and Effect

Since the device 110 has, in the inside of the second portion 12 of the tube 10, the first plug 31, the second plug 32, and the third plug 33 arranged in this order from the first portion 11 side of the tube 10, the time and effort required for pretreatment for PCR can be considerably reduced.

Specifically, in the second portion 12 of the tube 10, an oil, an eluate, and an oil are arranged in order in the form of plugs. Therefore, for example, if a specimen or the like is magnetic particles to which a target nucleic acid is adsorbed, the magnetic particles can be moved in the inside of the device 110, by applying a magnetic force from the outside of the device 110 in the first state, to be introduced via the tubular portion 21 of the plunger 20 into the second portion 12 of the tube 10, and the magnetic particles can be passed through the first plug 31 to move to the second plug 32 (eluate). Due to this, a nucleic acid extraction operation can be exactly performed in a short time while suppressing contamination. Moreover, the magnetic particles can be moved, as necessary, from the second portion 12 of the tube 10 to another portion with the device remaining in the first state. Thereafter, when the device 110 is brought into the second state and the plunger 20 is slid in the tube 10, the third plug 33 and the second plug 32 (eluate) can be discharged in this order from the second portion 12 side of the tube 10. Due to this, the effort to obtain an eluate containing nucleic acids at high purity can be considerably saved.

Moreover, when, like the device 110, the first plug 31, the second plug 32, and the third plug 33 are arranged in this order from the first portion 11 side of the tube 10 in the inside of the second portion 12 of the tube 10, the eluate is sealed by the plugs of oil in the tube 10. Therefore, even when the tip of the tube 10 on the second portion 12 side is opened in the atmosphere or the like, the evaporation of the eluate can be prevented. Due to this, for example, the volume of the eluate can be stabilized to be a predetermined size, so that the quantitation of the concentration of nucleic acid in the eluate can be maintained.

1.5.2. Container

Figure 6:
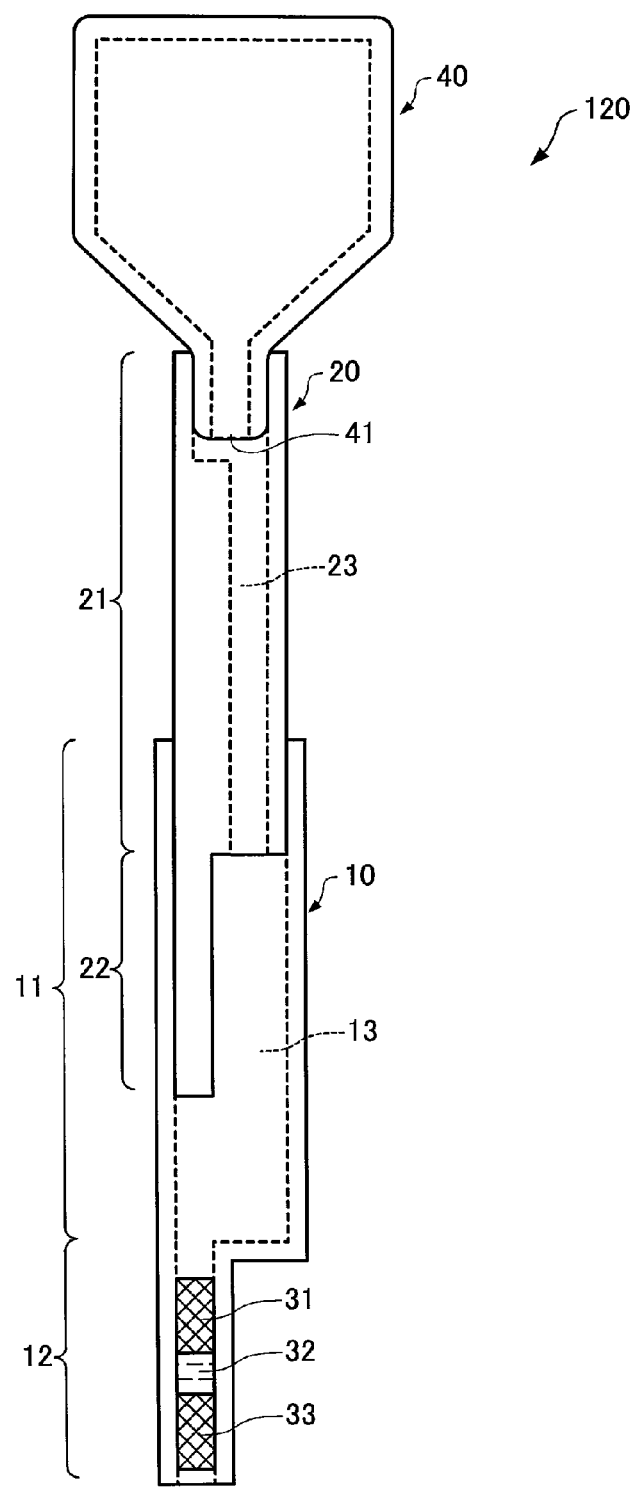
FIG. 6 schematically shows a device.

FIG. 6 schematically shows a device 120 as a configurational example of a device according to the embodiment of the invention. As illustrated as the device 120 in FIG. 6, a freely removable container 40 that can be connected to the end of the plunger 20 on the tubular portion 21 side, with the inside of the container being in communication with the inside of the tubular portion, may be further provided.

The container 40 can be an independent member. The container 40 can accommodate a liquid in the inside thereof. The container 40 has an opening 41 through which a liquid or solid can be taken in and out. Moreover, the example of FIG. 6 shows a form in which the opening 41 of the container 40 is connected to the end of the plunger 20 on the tubular portion 21 side with the inside of the container being in communication with the inside of the tubular portion. Moreover, although not illustrated, the container 40 may have a plurality of openings 41. In this case, a form may be adopted in which one of the openings 41 is connected to the end of the plunger 20 on the tubular portion 21 side with the inside of the container being in communication with the inside of the tubular portion.

Moreover, when, for example, the end of the plunger 20 on the tubular portion 21 side is sealed by a film or the like, connection can be made also by breaking through the film with a connection portion of the container 40 in connecting the container 40. To the contrary, when the opening 41 of the container 40 is sealed by a film or the like, connection can be made also by breaking through the film with the tubular portion 21 of the plunger 20 in connecting to the plunger 20.

The internal volume of the container 40 is not particularly limited, and can be, for example, from 0.1 mL to 100 mL. The opening 41 of the container 40 may be sealed, as necessary, by a lid or the like in a state of not being connected to the plunger 20. The material of the container 40 is not particularly limited, and can be a high polymer, a metal, or the like.

Although the opening 41 of the container 40 can be connected to the end of the plunger 20 on the tubular portion 21 side, the connection between the container 40 and the plunger 20 is not particularly limited as long as the contents do not leak. Moreover, the container 40 may include, for example, another member such as a joint, for being connected to the plunger 20. When the container 40 and the plunger 20 are connected to each other, the inside of the container 40 and the inside of the plunger 20 can be communicated with each other.

Since the device 120 includes the container 40, particles or the like, an adsorption solution, and a specimen, for example, can be accommodated in the container 40 and nucleic acids can be adsorbed to the particles or the like therein. When the container 40 is connected to the end of the plunger 20 on the tubular portion 21 side and the device 120 is brought into the first state, the particle or the like can be easily introduced into the second portion 12 of the tube 10 via the tubular portion 21 of the plunger 20.

The "adsorption solution" indicates a liquid in which nucleic acids are adsorbed to particles (magnetic particles M), and is, for example, an aqueous solution containing a chaotropic agent. A chelating agent, a surface-active agent, or the like may be contained in the adsorption solution. Specifically, disodium dihydrogen ethylenediaminetetraacetate, the dihydrate thereof, or the like may be dissolved in the adsorption solution, or polyoxyethylene sorbitan monolaurate or the like may be contained therein.

Moreover, the "chaotropic agent" indicates a substance that reduces interaction between water molecules to thereby make the water molecule structure unstable. Specifically, examples of chaotropic agents include a guanidinium ion, urea, and an iodide ion. Due to the presence of a chaotropic agent in water, nucleic acids in water are more thermodynamically advantageous when present adsorbed to a solid than when present surrounded by water molecules, and therefore, the nucleic acids are to be adsorbed onto the surfaces of particles or the like. Examples of substances that can generate a chaotropic agent in water include guanidine hydrochloride and sodium iodide.

The container 40 can be shaken in the state of not being connected to the tube 10, so that a liquid in the container 40 can be sufficiently stirred. Due to this, for example, nucleic acids can be adsorbed promptly to particles or the like.

Moreover, in the illustrated example, the plugs described above are arranged in the device 120. By doing this, nucleic acids in a specimen can also be concentrated quantitatively in the eluate of the second plug 32 by appropriately changing the amount of the specimen to be introduced into the container 40 and the volume of the liquid (particularly the second plug 32) in the tube 10.

Moreover, a mechanism for degassing (a valve or the like) (not shown) may be disposed in the container 40. Due to this, a rise in internal pressure can be suppressed in bringing the device 120 from the first state into the second state.

1.5.3. Stopper

Figure 7:
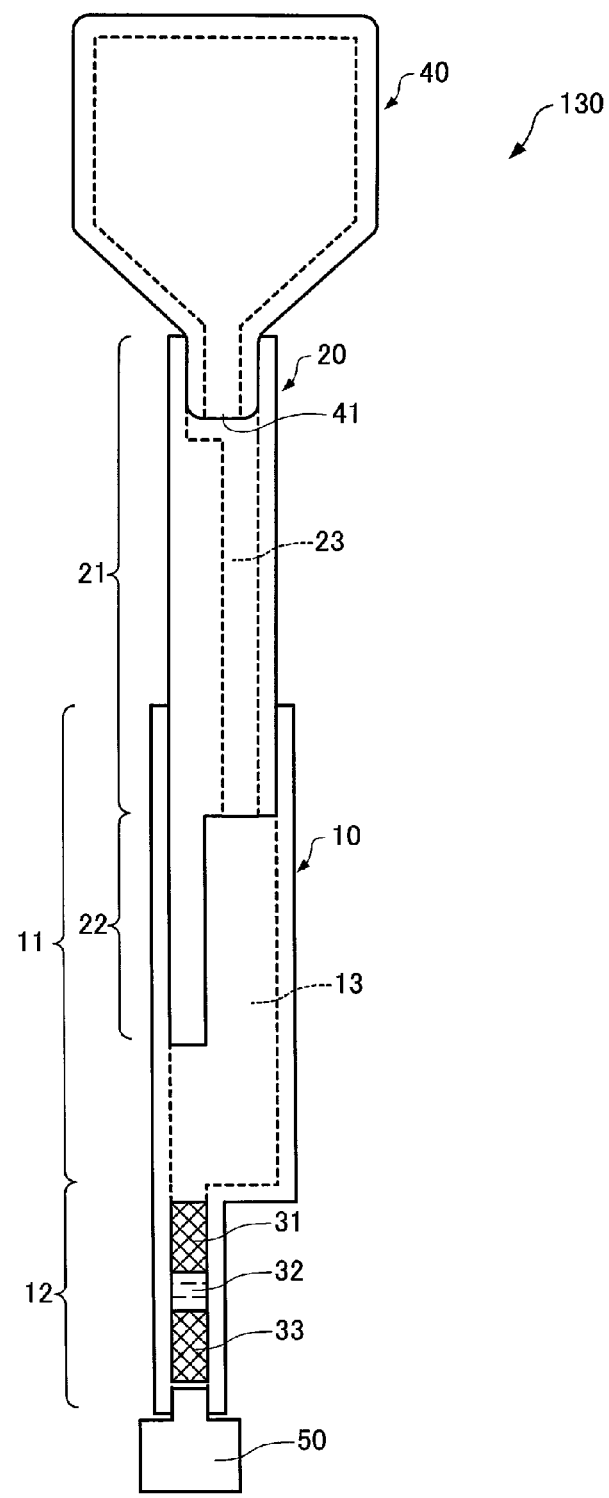
FIG. 7 schematically shows a device.

FIG. 7 schematically shows a device 130 according to the embodiment of the invention. The device 130 further has, as illustrated, a stopper 50 that seals the end of the tube 10 on the second portion 12 side. The stopper 50 can be formed of, for example, a molded body such as of a rubber, an elastomer, or a high polymer, a film, or the like. The stopper 50 may be in the form of a film, or may be in such a form that can be peeled off from a sealed state. When the tube 10 is sealed by the stopper 50, the stopper 50 may be in contact with the third plug 33, or a gas such as air may be arranged between the third plug 33 and the stopper 50. Moreover, although the stopper 50 can be freely movable, the mechanism thereof is not particularly limited. The example of FIG. 3 shows a form in which a portion of the stopper 50 is inserted and fixed into the inside of the tube 10. However, the stopper 50 may be in the form of a cap or in the form of a film.

When the stopper 50 is removed in the device 130, the end of the tube 10 on the second portion 12 side is opened and the device 130 is brought into the above form of the device 120 in FIG. 6. Therefore, when the device 130 includes the plugs as illustrated, the eluate (the second plug 32) containing a target nucleic acid can be easily dispensed into, for example, a reaction container for PCR or the like. Moreover, when the device 130 is in a state where the end of the tube 10 on the second portion 12 side is sealed by the stopper 50 (the state shown in FIG. 7), an advantageous effect of suppressing the movement of each of the plugs in the tube 10 is obtained. Due to this, when, for example, particles or the like is moved in the tube 10 or the state of the device 130 is changed between the first state and the second state, the movement of the plugs can be suppressed.

1.6. Configuration Having Plurality of Devices

Figure 8:
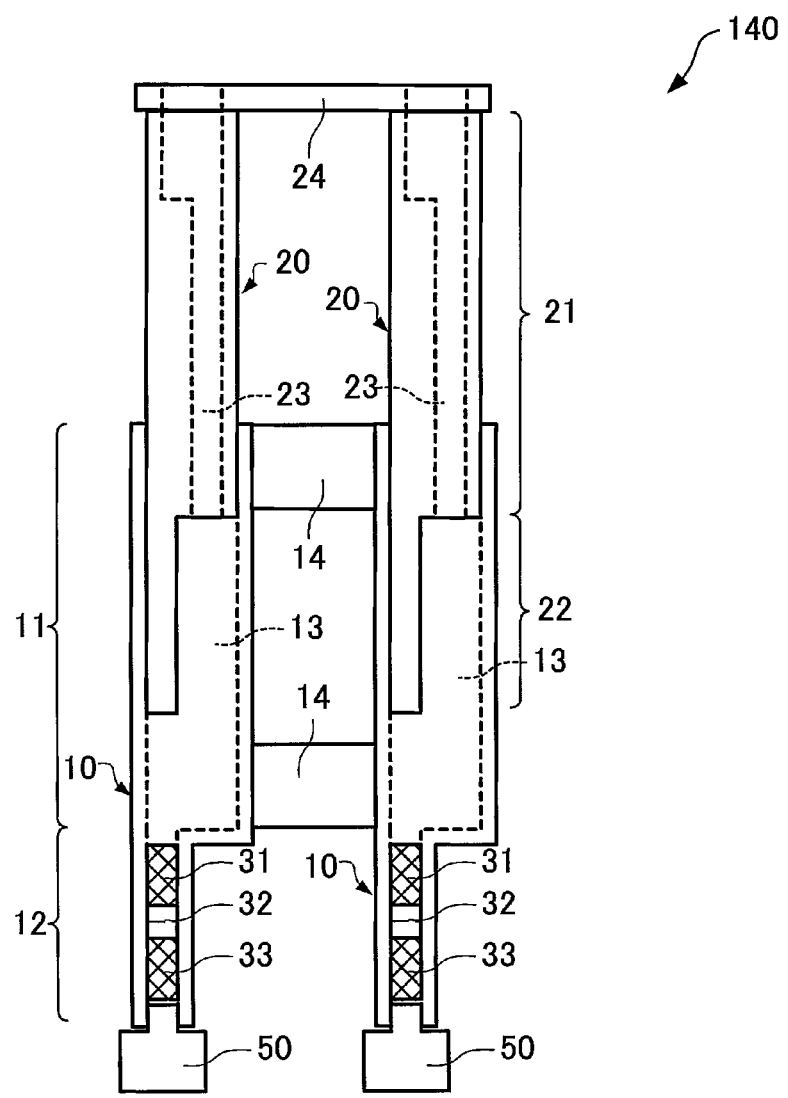
FIG. 8 schematically shows a device.

A device according to the embodiment may be configured to have a plurality of the tubes 10 and a plurality of the plungers 20 described above. FIG. 8 is a schematic view showing a device 140 having two tubes 10 and two plungers 20.

The two tubes 10 are arranged with their longitudinal directions being parallel to each other, and coupled with each other through coupling members 14. Moreover, the two plungers are arranged with their longitudinal directions being parallel to each other, and coupled with each other through a coupling member 24. By arranging them in this manner, the two plungers 20 can be slid in conjunction with each other in the two respectively corresponding tubes 10. The structures, functions, materials, modifications, and the like of the tubes 10 and the plungers 20 are similar to those described above, and therefore, the detailed description is omitted.

The example of FIG. 8 shows an example in which two tubes 10 and two plungers 20 are provided. However, the number of pairs of the tube 10 and the plunger 20 is not limited, and may be three or more. Moreover, when three or more tubes 10 and three or more plungers 20 are provided, any form in which they are arranged parallel to each other is available. They may be arranged such that their longitudinal directions share one plane, or they may be arranged in a matrix (two-dimensionally) as viewed from the longitudinal direction.

The plurality of plungers 20 and the plurality of tubes 10 operate in conjunction with each other. Therefore, the pairs each composed of the tube 10 and the plunger 20 can simultaneously form the first state and the second state described above.

According to the device 140, arrangements of the plurality of tubes 10 and the plurality of plungers 20 can be simultaneously brought into the first state, and in that state, a specimen or the like can be introduced into the second portion 12 of each of the tubes 10 via the tubular portion 21 of each of the plungers 20. Then, the arrangements of the plurality of tubes 10 and the plurality of plungers 20 can be simultaneously shifted from the first state to the second state, and thus, it is possible to constitute a syringe in the second portion 12 of each of the tubes 10. Therefore, the specimen can be distributed with a simple operation while suppressing contamination of the specimen or the like, so that a plurality of reaction solutions of PCR can be manufactured in an easy manner.

Moreover, the tubes 10 and the plungers 20 can be operated in conjunction with each other. Therefore, the specimen or the like can be exactly discharged from the second portion 12 of each of the tubes 10, so that the specimen or the like can be dispensed at a substantially equal amount into each of a plurality of containers or the like. Hence, according to the device 140, pretreatment of PCR, for example, can be performed in more simple and precise manners, and moreover, the time required for PCR can be further shortened.

Figure 9:
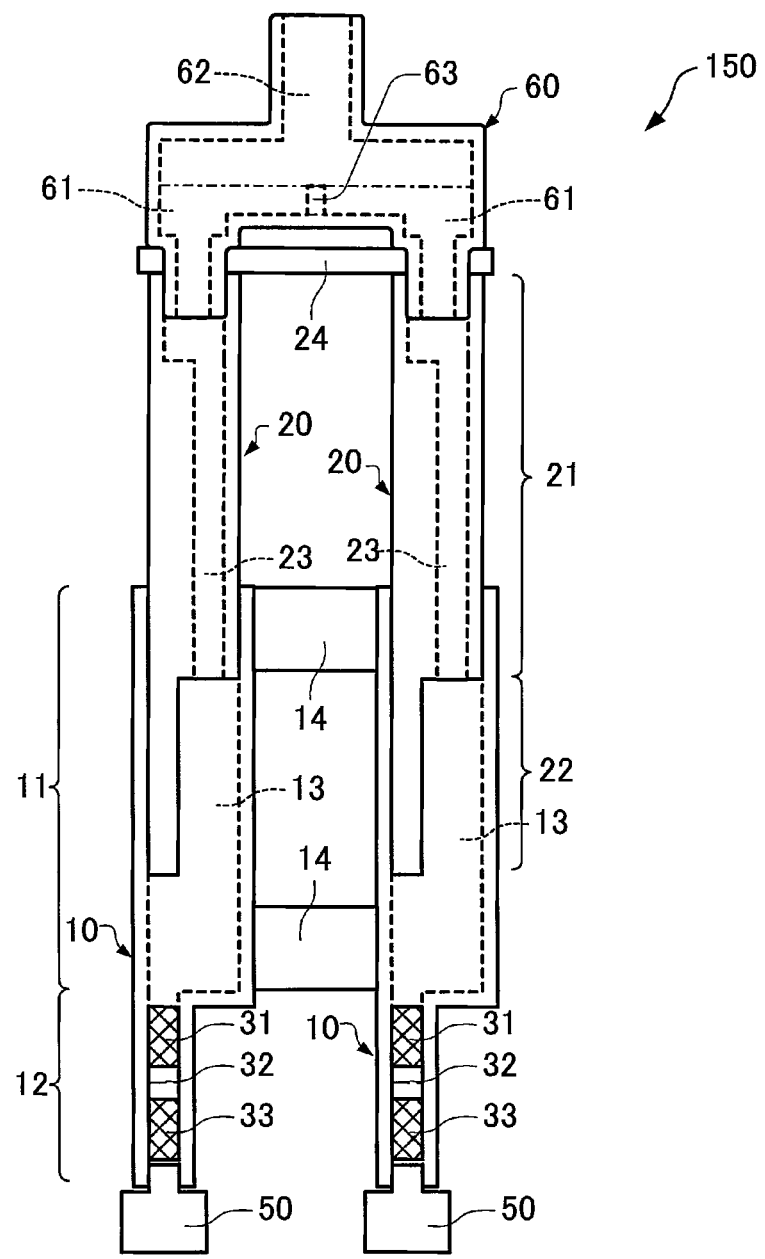
FIG. 9 schematically shows a device.

FIG. 9 is a schematic view showing a device 150 having two tubes 10 and two plungers 20 and further including a manifold 60 connectable to the tubular portions 21 of the two plungers 20.

When the manifold 60 is connected to the tubular portions 21 of the two plungers 20, the insides of the tubular portions 21 and the inside of the manifold 60 can be communicated with each other. Then, the manifold 60 can have a plurality of individual passages 61 each connected to the tubular portion 21 and a common passage 62 connected to the individual passages 61 to join them to one.

Herein, an example of having two individual passages 61 is shown. However, similarly as described in the device 140, three or more individual passages 61 may be disposed according to the number of the plungers 20.

According to the device 150, since the manifold 60 is provided, particles or the like can be introduced from one common passage 62 into the tubular portions 21 of the plungers 20 by separating the particles or the like into the individual passages 61. Therefore, since in PCR for example, a reaction solution or the like can be dispensed at a time into a plurality of reaction containers, the time required for PCR can be further shortened.

Moreover, the volumes of the plurality of individual passages 61 of the manifold 60 can be made substantially equal to each other. The volumes of the plurality of individual passages 61 can be made substantially equal to each other by, for example, making the length of a partition 63 uniform, which partitions between the individual passages 61, from the plunger 20 and making the inside diameters of the individual passages 61 substantially equal to each other.

By doing this, when a liquid is introduced from the common passage 62, a liquid of a substantially equal volume can be easily distributed to each of the plungers 20. Specifically, when, for example, a liquid is introduced from the common passage 62 in a state where the manifold 60 is connected to the plungers 20, top surfaces of liquids introduced into the individual passages 61 are made to have the same level visually by, for example, tilting the device 150, whereby the liquid of a substantially equal volume can be distributed to each of the individual passages 61.

Here, in the case where the rod-like portion 22 is not present in the device 150, when the plunger 20 is pushed into each of the tubes 10, pressures are evenly applied in the tubes 10. However, since resistance for a liquid to flow is present in the second portion 12 of the tube 10 and a pressure is applied to the plurality of tubes 10, the flow is first generated in any of the tubes 10 in some cases due to a small difference in resistance. Then, a pressure in the tube 10 other than the tube 10 in which the flow was generated is relatively lowered, and therefore, discharge from another tube 10 is not performed or discharge becomes unstable in some cases. In contrast to this, when the rod-like portion 22 is disposed in each of the plungers 20 like the device 150, a pressure can be evenly applied to each of the tubes 10 mechanically independent of each other, and therefore, discharge of the contents from each of the tubes 10 can be performed very precisely.

Although not illustrated, the device 150 may further include the container 40 connectable to the common passage 62 of the manifold 60. The container 40 is similar to the container 40 described in "1.5.2. Container". In this case, the opening 41 of the container 40 is connected to the common passage 62 of the manifold 60 with the inside of the container being in communication with the inside of the common passage 62. Then, when the container 40 is connected to the manifold 60 and the device 150 is brought into the first state, the particles or the like can be introduced into each of the tubes 10.

2. Specific Example of Device

Figure 10:
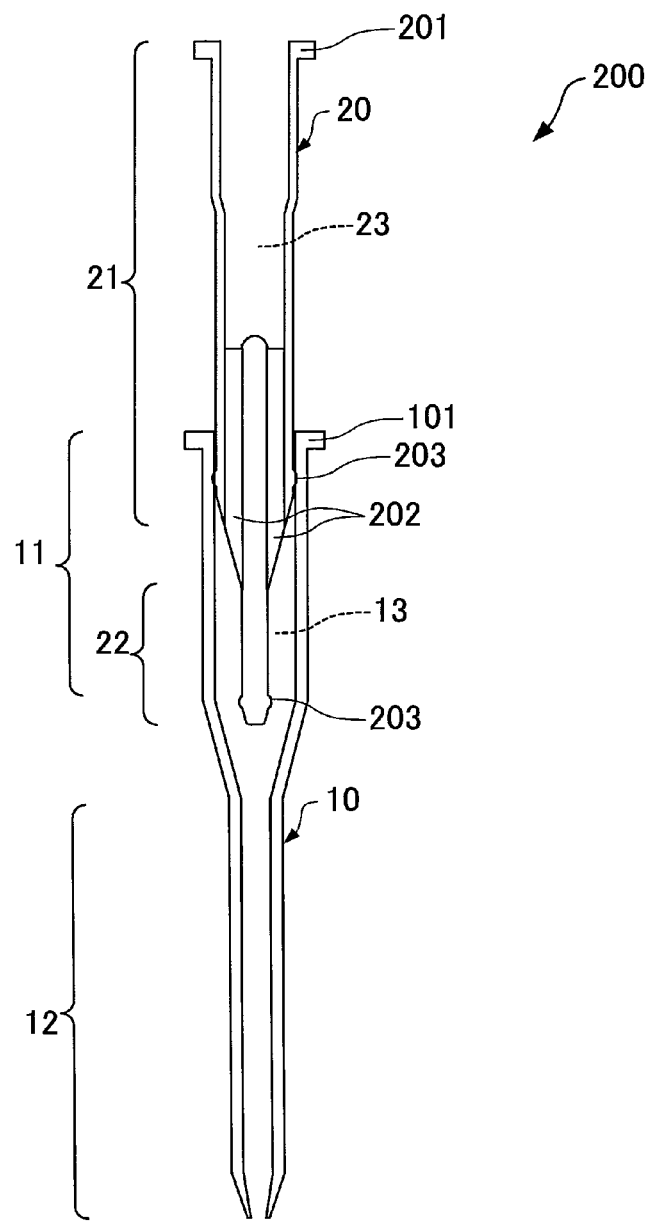
FIG. 10 schematically shows a first state of a device.
Figure 11:
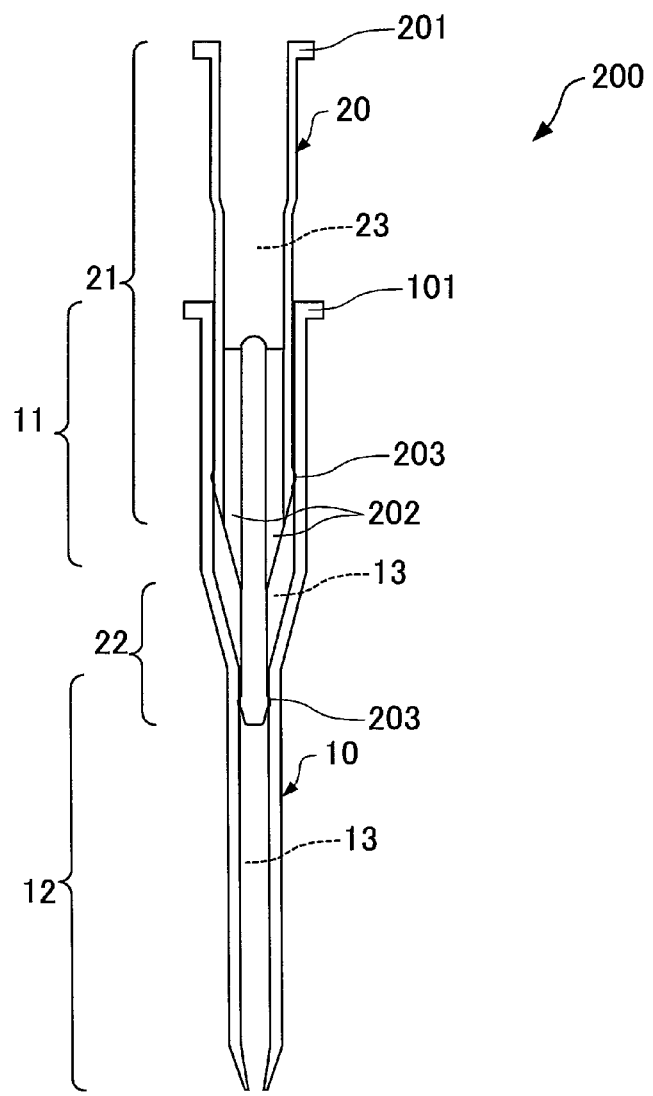
FIG. 11 schematically shows a second state of the device.

Next, a more specific example of a device according to the invention will be described. As one embodiment of the specific example according to the invention, a device 200 shown below will be illustrated. The device 200 includes the tube 10 and the plunger 20. FIGS. 10 and 11 schematically show the device 200 forming the first state and the second state, respectively. In this section, members having actions and functions similar to those described in the section of "1. Device" are denoted by similar reference signs and numerals, and the detailed description thereof is omitted.

2.1. Tube

Although the tube 10 in the device 200 is similar to that described in the section of "1. Device", the shape of a cross-section of the inner cavity 13 of the tube 10, where the cross-section is perpendicular to the longitudinal direction, is a circle in the examples shown in FIGS. 10 and 11. Moreover, the shape of a cross-section of an external form of the tube 10 in the device 200, where the cross-section is normal to the longitudinal direction, is a circular shape, and the wall thickness (length from the side surface to the outer surface of the inner cavity 13) of the tube 10 is substantially constant, excepting the tip of the second portion 12. Moreover, in the tube 10 in the device 200, an edge portion 101 is formed at the end on the first portion 11 side. The edge portion 101 has the actions of easing the handling of the tube 10 and increasing the strength of the tube 10.

The material of the tube 10 in the device 200 is a high polymer (polypropylene). When, for example, magnetic particles are caused to pass through the tube 10, the magnetic particles can be moved by giving a magnetic force from the outside of the tube 10. Moreover, the tube 10 can be formed by injection molding. In the illustrated device 200, the tube 10 shows an example of a shape easy to remove from a mold.

In the tube 10 in the device 200, the first portion 11 and the second portion 12 are spaced apart from each other, and a tapered portion is formed and connected therebetween. Then, similarly as described in the section of "1. Device", the device 200 has a structure in which in the state where the tubular portion 21 of the plunger 20 fits the inner surface of the first portion 11 of the tube 10, the plunger 20 can be slid relative to the tube 10 while being in close contact therewith. Moreover, in the tube 10 in the device 200, the inner cavity 13 of the second portion 12 is connected relative to the inner cavity 13 of the first portion 11 with their centers coinciding with each other.

2.2. Plunger

The plunger 20 in the device 200 is similar to that described in the section of "1. Device". However, in the example shown in FIG. 10, the plunger 20 has the tubular portion 21 and the rod-like portion 22, and the rod-like portion 22 is supported by two support portions 202 relative to the tubular portion 21. Also in this example, the inner cavity 23 penetrating in the longitudinal direction is formed in the tubular portion 21 of the plunger 20. The tubular portion 21 and the rod-like portion 22 of the plunger 20 in the device 200 can internally contact the first portion 11 and the second portion 12 of the tube 10 but each have a convex portion 203 that has the action of a gasket. In the device 200, since the convex portions 203 are formed, leakage of a liquid or the like in the inside can be more reduced.

The shape of a cross-section of each of the tubular portion 21 and the rod-like portion 22 of the plunger 20 in the device 200, where the cross-section is perpendicular to the longitudinal direction, is a circular shape, and the tubular portion 21 and the rod-like portion 22 can fit the inner walls of the first portion 11 and the second portion 12 of the tube 10. In the plunger 20 in the device 200, an edge portion 201 is formed at the end on the tubular portion 21 side. The edge portion 201 has the actions of easing handling of the plunger 20 and increasing the strength of the plunger 20.

The material of the plunger 20 in the device 200 is a high polymer (polypropylene). Moreover, the plunger 20 can be formed by injection molding. The plunger 20 in the device 200 shows an example of a shape easy to remove, from a mold, the plunger 20 including the edge portion 201, the support portions 202, and the convex portions 203. In the device 200, the tubular portion 21, the rod-like portion 22, the edge portion 201, the support portions 202, and the convex portions 203 of the plunger 20 are integrally formed of the same material.

2.3. Positional Relation Between Tube and Plunger

FIG. 10 shows the device 200 arranged in the first state. FIG. 11 is a schematic view showing the device 200 arranged in the second state.

Similarly as described in the section of "1. Device", the plunger 20 can be inserted into the tube 10 from the first portion 11 side of the tube 10 with the rod-like portion 22 as the tip, also in the device 200. When the plunger 20 is inserted, the tubular portion 21 of the plunger 20 first fits the inner surface of the first portion 11 of the tube 10. Then, when the plunger 20 is further inserted into the tube 10, the state where the rod-like portion 22 of the plunger 20 fits the inner surface of the second portion 12 of the tube 10 is formed. That is to say, the device 200 according to the embodiment can adopt the first state illustrated in FIG. 10 and the second state illustrated in FIG. 11.

Also in the device 200, when the first state is adopted, a space communicating from the outside world via the tubular portion 21 of the plunger 20 to the inside of the second portion 12 of the tube 10 can be formed. Moreover, also in the device 200, when the second state is adopted, the rod-like portion 22 of the plunger 20 and the second portion 12 of the tube 10 can constitute a syringe.

2.4. Other Configurations

Similarly to the device 100 described in the description of the section of "1. Device", the device 200 may include, in addition to the tube 10 and the plunger 20, various configurations such as a plug, a container, and a stopper, and these configurations can be applied in combination.

2.5. Configuration Having Plurality of Devices

Figure 12:
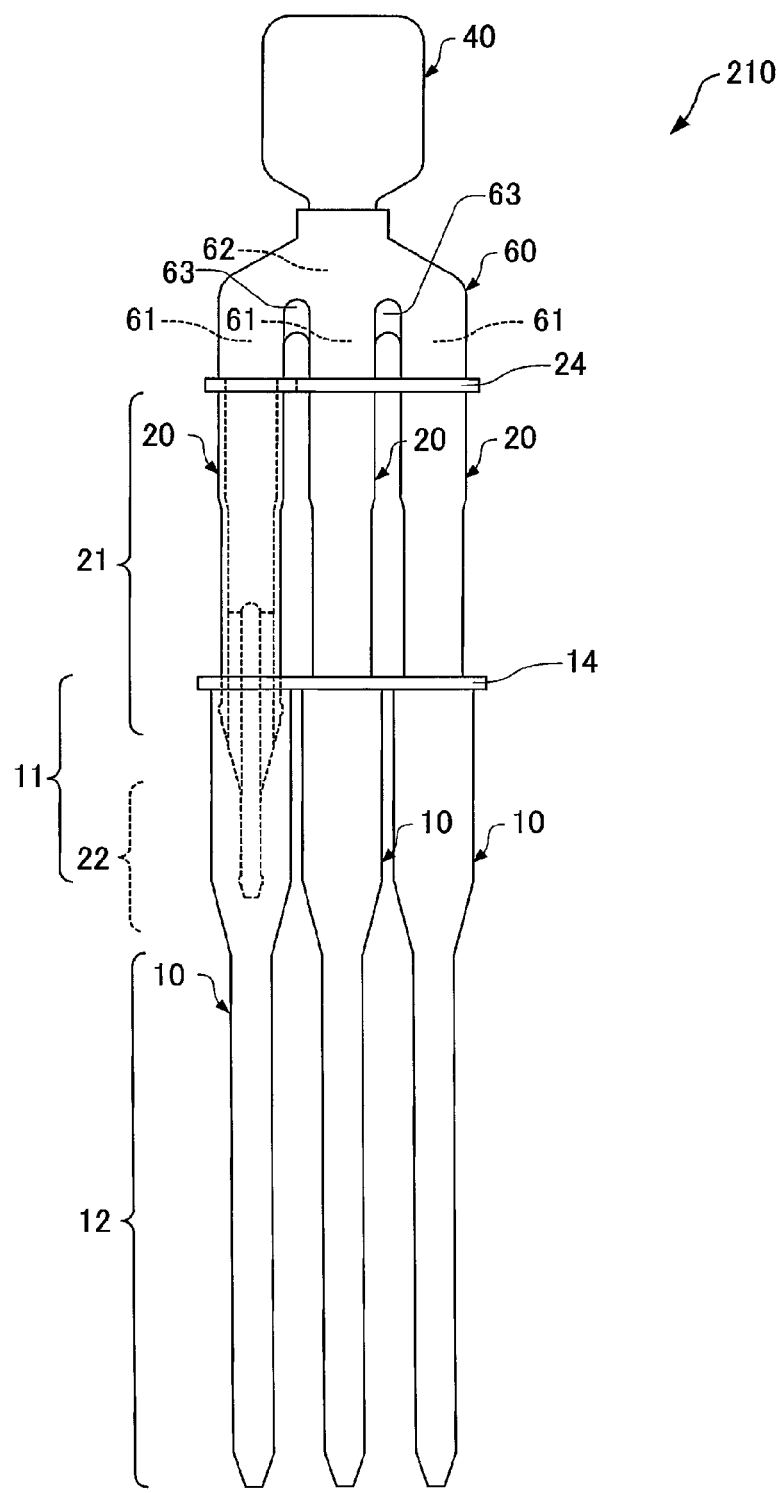
FIG. 12 schematically shows a first state of a device.
Figure 13:
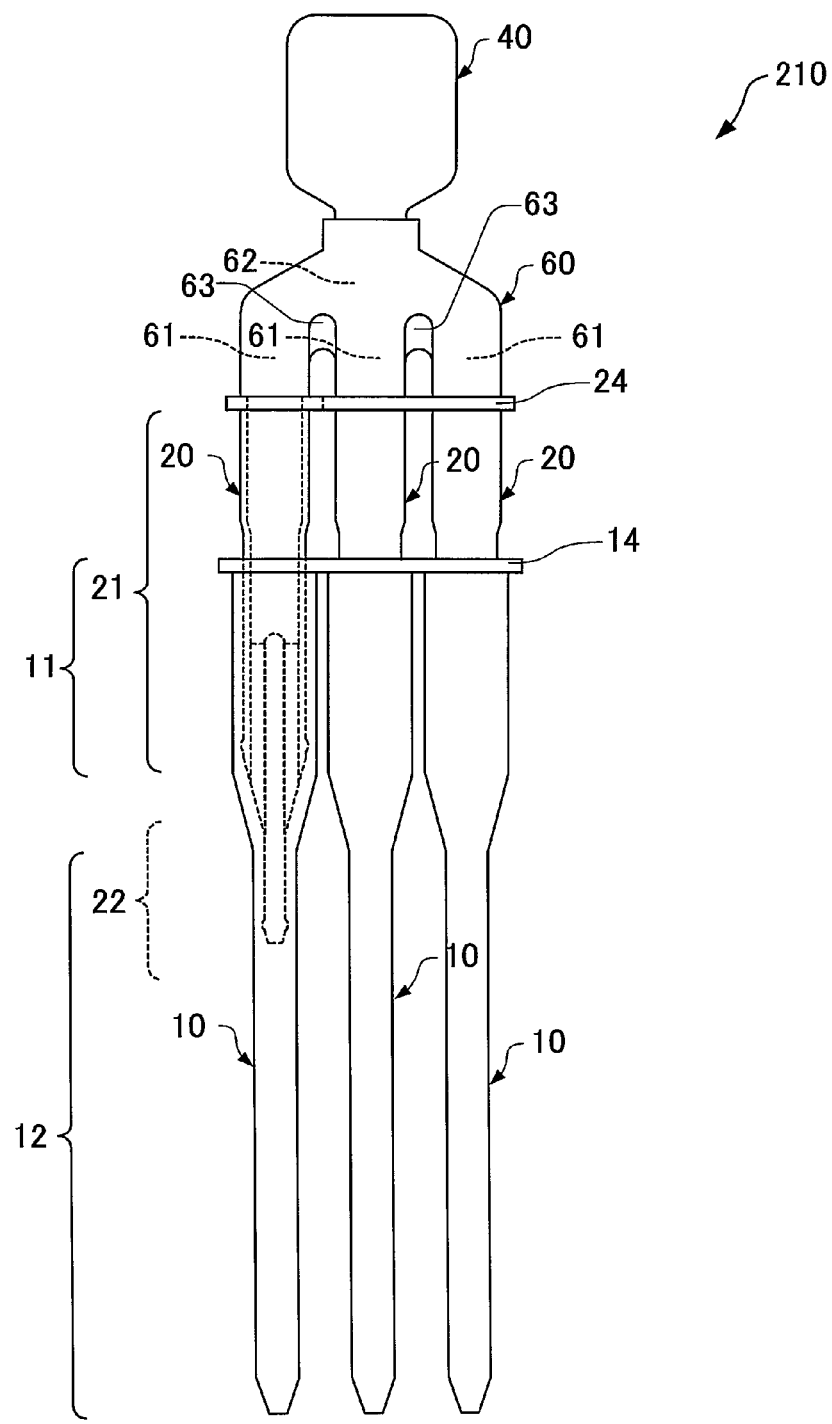
FIG. 13 schematically shows a second state of the device.

FIGS. 12 and 13 are schematic views showing a device 210 having three tubes 10 and three plungers 20. Since the structures, functions, materials, modifications, and the like of the tubes 10 and the plungers 20 are similar to those of the devices 140 and 150 described above, similar members are denoted by similar reference signs and numerals, and the detailed description is omitted. Moreover, FIGS. 12 and 13 schematically show the device 210 adopting the first state and the second state, respectively.

Since the plurality of plungers 20 and the plurality of tubes 10 operate in conjunction with each other, the pairs each composed of the tube 10 and the plunger 20 can adopt, in synchronization with each other, the first state and the second state.

FIGS. 12 and 13 show the device 210 having the plurality of tubes 10 and the plurality of plungers 20, and further including the manifold 60 connectable to the tubular portions 21 of the plurality of plungers 20 and the container connectable to the common passage 62 of the manifold 60.

When the manifold 60 is connected to the tubular portions 21 of the plurality of plungers 20, the insides of the tubular portions 21 and the inside of the manifold 60 can be communicated with each other. Then, the manifold 60 can have the plurality of individual passages 61 each connected to the tubular portion 21 and the common passage 62 connected to the individual passages 61 to join them to one.

According to the device 210, since the manifold 60 is provided, particles or the like can be introduced from one common passage 62 into the tubular portions 21 of the plungers 20 by separating the particles or the like into the individual passages 61. Therefore, since in PCR for example, a reaction solution or the like can be distributed and dispensed at a time into a plurality of reaction containers, the time required for PCR can be further shortened.

Further, according to the device 210, the second state is simultaneously formed relative to the tubes 10, and the rod-like portions 22 can be slid in conjunction with each other. Therefore, discharge of the contents from each of the tubes 10 can be exactly performed. In other words, in the case where the rod-like portion 22 is not present in the device 210, when the plunger 20 is pushed into each of the tubes 10, pressures are evenly applied in the tubes 10. However, since resistance for a liquid to flow is present in the second portion 12 of the tube 10 and a pressure is applied to the plurality of tubes 10, the flow is generated in any of the tubes 10 in some cases due to a small difference in resistance. Then, a pressure in the tube 10 other than the tube 10 in which the flow was generated is relatively lowered, and therefore, discharge from another tube 10 becomes unstable in some cases. In contrast to this, when the rod-like portion 22 is disposed in each of the plungers 20 like the device 210, a pressure can be evenly applied to each of the tubes 10 independently of each other, and therefore, discharge of the contents from each of the tubes 10 can be precisely performed.

Moreover, the volumes of the plurality of individual passages 61 of the manifold 60 can be made substantially equal to each other. The volumes of the plurality of individual passages 61 can be made substantially equal to each other by, for example, making the lengths of the partitions 63 uniform, each of which partitions between the individual passages 61, from the plunger 20 and making the inside diameters of the individual passages 61 substantially equal to each other.

By doing this, when a liquid is introduced from the common passage 62, a liquid of a substantially equal volume can be easily distributed to each of the plungers 20. Specifically, when, for example, a liquid containing magnetic particles to which nucleic acids are adsorbed is introduced from the common passage 62 in a state where the manifold 60 is connected to the plungers 20, top surfaces of liquids introduced into the individual passages 61 are made to have the same level visually by, for example, tilting the device 210, whereby the liquid of a substantially equal volume can be distributed to each of the individual passages 61.

Further, as shown in FIGS. 12 and 13, the container 40 connectable to the common passage 62 of the manifold 60 may be further included. The container 40 is similar to the container 40 described in "1.5.2. Container". In this case, the opening of the container 40 is connected to the common passage 62 of the manifold 60 with the inside of the container being in communication with the inside of the common passage. Then, when particles or the like and a specimen are accommodated in the container 40, nucleic acids can be adsorbed to the particles or the like in the container 40. When the container 40 is connected to the manifold 60 and the device 210 is brought into the first state, the particles or the like can be introduced into each of the tubes 10.

3. Method of Using Device

Hereinafter, a nucleic acid extraction method for performing pretreatment of PCR (nucleic acid extraction and dispensing of a reaction solution of PCR) using a device including the container 40, the first plug 31, the second plug 32, and the third plug 33 will be illustrated as one embodiment.

FIGS. 14A to 15I schematically show steps of the nucleic acid extraction method using the device. The pretreatment method of PCR illustrated herein includes a step of introducing a specimen containing nucleic acids into the container 40 in which the magnetic particles M and an adsorption solution are accommodated, a step of rocking the container 40 to adsorb the nucleic acids to the magnetic particles M, a step of connecting the container 40 to the end of the plunger 20 on the tubular portion 21 side, a step of applying a magnetic force to move the magnetic particles M from the inside of the container 40 through the inside of the tubular portion 21 of the plunger 20 to the position of the second plug 32 of the tube 10, and a step of eluting the nucleic acids from the magnetic particles M into the eluate of the second plug 32.

As the particles to which nucleic acids are adsorbed, various (for example, silica particles, polymer particles, magnetic particles, or the like) particles can be used as long as the particles can adsorb nucleic acids with an adsorption solution and the particles can move in the device. In one embodiment of the nucleic acid extraction method described below, the magnetic particle M that contains a magnetic substance and can adsorb nucleic acids on its particle surface is used. When particles or the like other than the magnetic particles M is caused to move in the device, the nucleic acid extraction method can be performed using, for example, gravity or a potential difference.

In the nucleic acid extraction method of the embodiment, a material that transmits a magnetic force is selected for the container 40, the plunger 20, and the tube 10, and the magnetic force is applied from the outside, whereby the magnetic particles M are caused to move in the inside of the device 200.

A nucleic acid as a target is contained in a specimen. Hereinafter, this is sometimes simply referred to as "target nucleic acid". The target nucleic acid is, for example, DNA or RNA (deoxyribonucleic acid and/or ribonucleic acid). The target nucleic acid is extracted from a specimen by the nucleic acid extraction method of the embodiment, eluted into an eluate, and then used as, for example, a template of PCR. Examples of specimens include blood, nasal mucus, oral mucosa, and other various biological samples.

3.1. Step of Introducing Specimen into Container

The step of introducing a specimen into the container 40 can be performed by, for example, applying the specimen to a cotton swab, inserting the cotton swab from the opening 41 of the container 40, and immersing the cotton swab in an adsorption solution. Moreover, the specimen may be introduced from the opening 41 of the container 40 with a pipette or the like. Moreover, when the specimen is in the form of a paste or the form of a solid, the specimen may be, for example, applied to an inner wall of the container 40, or may be charged through the opening 41 of the container 40 with a spoon, tweezers, or the like. FIG. 14A shows a state where the opening 41 of the container 40 is sealed by a film 43. In this step, the film is peeled off, and the specimen is introduced as schematically shown by an arrow in FIG. 14C.

3.2. Step of Adsorbing Nucleic Acids to Magnetic Particles

The step of adsorbing nucleic acids is performed by rocking the container 40. That is, this step is performed by rocking the container 40 in a state shown in FIG. 14C. If a lid or the like that seals the opening 41 of the container 40 is present, this step is performed by sealing the container 40 using the lid or the like, whereby leakage can be prevented to efficiently perform this step. Through this step, the target nucleic acid is adsorbed to the surfaces of the magnetic particles M by the action of a chaotropic agent. In this step, in addition to the target nucleic acid, nucleic acids other than the target nucleic acid or proteins may be adsorbed to the surfaces of the magnetic particles M.

As a method of rocking the container 40, an apparatus such as a vortex shaker may be used, or a worker may shake with his/her hand the container 40 for mixing. Moreover, with the use of magnetism of the magnetic particles M, the container 40 may be rocked while giving a magnetic field from the outside. The time for rocking the container 40 can be appropriately set. When, for example, the approximate shape of the container 40 is in the form of a circular cylinder with a diameter of 20 mm and a height of about 30 mm, the liquid is sufficiently stirred by simply rocking the container 40 by shaking with a hand for 10 seconds, so that nucleic acids can be adsorbed to the surfaces of the magnetic particles M.

3.3. Step of Connecting Container to Plunger

Next, as shown in FIG. 14D, the container 40 is connected to the end of the plunger 20 on the tubular portion 21 side. This example shows an example in which the connection is made in a state where the plunger 20 is inserted into the tube 10. However, the container 40 may be connected to the plunger 20 in a state where the plunger 20 is not inserted into the tube 10, so as to avoid leakage of the liquid in the container 40. Moreover, in the examples shown in FIGS. 14A to 14E, a nipple 42 is connected to the container 40, so that the container 40 is connected to the plunger 20 via the nipple 42.

When performing of this step causes a risk of moving the plugs in the tube 10, the stopper 50 may be disposed in the tube 10, or a valve or the like (not shown) that relieves the internal pressure of the device may be disposed, to perform this step. Moreover, for the plugs in the tube 10, there is resistance to flow in the second portion 12 of the tube 10. Therefore, the plugs are unlikely to move with an increase in internal pressure caused by simply connecting the container 40, so that the stopper 50, or a valve or the like is not necessarily indispensable. The container 40 and the plunger 20 are connected so as to avoid leakage of the contents, and communicated with each other such that the contents can flow between the inside of the container 40 and the inside of the plunger 20.

3.4. Step of Moving Magnetic Particles

Through the steps described above, as shown in FIG. 14D, a state where the magnetic particles M to which the nucleic acids are adsorbed in the container 40 can flow into the tubular portion 21 of the plunger 20 is established. This step is performed with the device being in the first state. That is, this step is performed in a state where the inside of the container 40, the inside of the tubular portion 21 of the plunger 20, and the inside of the second portion 12 of the tube 10 are spatially communicated with each other.

As a method of introducing the magnetic particles M to which the nucleic acids are adsorbed from the container 40 via the tubular portion 21 of the plunger 20 to the second portion 12 of the tube 10, a method of using gravity or centrifugal force may be used, and the method is not particularly limited. In the embodiment, however, the introduction is performed by applying a magnetic force from the outside of the device. Although the magnetic force can be applied using, for example, a permanent magnet, an electromagnet, or the like, the magnetic force can be more preferably applied using a permanent magnet in view of not causing heat generation or the like. In the illustrated example, a permanent magnet 70 is used. Moreover, when the permanent magnet 70 is used, the magnet may be moved with a worker's hand or using a mechanical apparatus or the like. Since the magnetic particle M has a property of being attracted by a magnetic force, a relative arrangement of the device and the permanent magnet 70 is changed using this property to move the magnetic particle M from the inside of the container 40 to the second portion 12 of the tube 10. Due to this, the magnetic particles M are moved through the first plug 31 to the second plug 32 as shown in FIG. 14E. The time for the magnetic particles M to stay in the first plug 31 during passing through the first plug 31 is not particularly limited, and the magnetic particles M may be moved in the second plug 32 so as to reciprocate along the longitudinal direction of the tube 10.

3.5. Step of Eluting Nucleic Acids

When the magnetic particles M reach the second plug 32, the nucleic acids adsorbed to the magnetic particles M are eluted into the eluate of the second plug 32 with the action of the eluate. Through this step, the nucleic acids are eluted from the specimen into the eluate, so that a state where the nucleic acids are extracted from the specimen is established.

3.6. Action and Effect

According to the nucleic acid extraction method of the embodiment, the nucleic acid extraction can be easily performed in an extremely short time. In the nucleic acid extraction method of the embodiment, the magnetic particles M to which nucleic acids are adsorbed are moved in the device, whereby an eluate containing nucleic acids at high purity can be obtained. According to the nucleic acid extraction method of the embodiment, the time and effort required for pretreatment for PCR can be considerably reduced.

3.7. Step of Discharging Second Plug from Tube

Figure 15F:
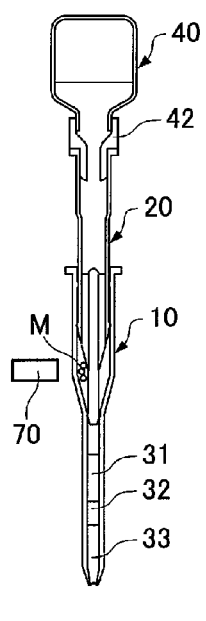
FIGS. 15F to 15I schematically show steps of the nucleic acid extraction method using the device.

The nucleic acid extraction method of the embodiment may include a step of discharging the third plug 33 and the second plug 32 from the end of the second portion 12 of the tube 10 after bringing the device into the second state. This step can be performed, after "3.5. Step of Eluting Nucleic Acids", by bringing the device into the second state as shown in FIG. 15F and pushing the plunger 20 into the tube 10 (sliding the plunger 20 relative to the tube 10) in a state where the rod-like portion 22 of the plunger 20 and the second portion 12 of the tube 10 form a syringe. When the second plug 32 is discharged, the third plug 33 is first discharged. When the stopper 50 that seals the second portion 12 side of the tube 10 is present, the stopper 50 is removed prior to this step to open the end of the tube 10 on the second portion 12 side.

Figure 15G:
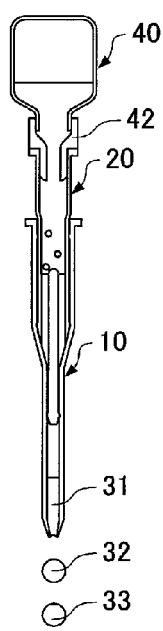

Then, as shown in FIG. 15G, when the plunger 20 is slid relative to the tube 10 in the second state, the plugs arranged in the second portion 12 of the tube 10 move toward the other end side of the tube 10. Due to this, the third plug 33 and the second plug 32 are discharged in this order from the end of the tube 10 on the second portion 12 side. The first plug 31 may or may not be discharged.

The second plug 32 and the third plug 33 are discharged into, for example, a reaction container for PCR. Therefore, the eluate and the oil are dispensed into the reaction container for PCR. However, since an oil does not usually affect a PCR reaction, an oil of the same kind as the oil of the third plug 33 can be previously accommodated in, for example, the reaction container of PCR. Moreover, in that case, when this step is performed in a state where the tip of the tube 10 is located in the oil, the eluate containing the target nucleic acid can be introduced into the reaction container of PCR without contacting outside air. When the nucleic acid extraction method of the embodiment includes this step, the eluate containing the target nucleic acid can be easily dispensed into, for example, the reaction container of PCR, or the like.

3.8. Modified Examples 3.8.1. Modification of Step of Eluting Nucleic Acids

In "3.5. Step of Eluting Nucleic Acids" described above, the step may be performed by heating the second plug 32. Examples of methods of heating the second plug 32 include, for example, a method of bringing a heat medium such as a heat block into contact with the tube 10 at a position corresponding to the second plug 32, a method of using a heat source such as a heater, and a method of using electromagnetic heating.

When the second plug 32 is heated, the plugs other than the second plug 32 may also be heated. However, when the device includes a cleaning fluid, the plugs may not be preferably heated in a state where the magnetic particles M to which the nucleic acids are adsorbed are present in the cleaning fluid. The achieving temperature in the case of heating the second plug 32 is preferably from 35° C. to 85° C., more preferably from 40° C. to 80° C., and further preferably from 45° C. to 75° C. from the standpoint of elution efficiency and the standpoint of suppressing, in the case where the eluate contains an enzyme of PCR, deactivation of the enzyme.

When the second plug 32 is heated in the step of eluting nucleic acids, the nucleic acids adsorbed to the magnetic particles M can be more efficiently eluted into the eluate. Moreover, even when the composition of a cleaning fluid is the same as or similar to that of the eluate, nucleic acids not eluted into the cleaning fluid but remain adsorbed to the magnetic particles M can be eluted into the eluate. That is, even after cleaning the magnetic particles M to which nucleic acids are adsorbed with the cleaning fluid, the nucleic acids can be further eluted into the eluate. Due to this, even when the composition of the cleaning fluid is the same as or similar to that of the eluate, sufficient cleaning is compatible with the elution of nucleic acids at a sufficient concentration into the eluate.

3.8.2. Modification of Step of Discharging Second Plug from Tube

Figure 15H:
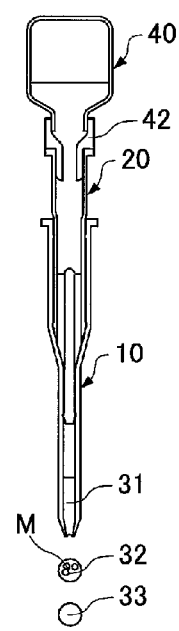
Figure 15I:
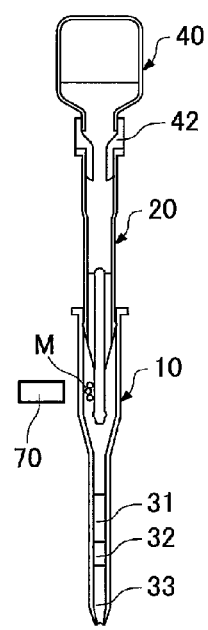

When "3.7. Step of Discharging Second Plug from Tube" described above is adopted, the magnetic particles M that have completed the elution of nucleic acids into the eluate may be discharged in the step together with the eluate, as shown in FIG. 15H, unless it affects a PCR reaction. However, the magnetic particles M may be moved, in the first state by further applying a magnetic force, to the inside of the first plug 31, to a closer position on the container 40 side than the second portion 12 of the tube 10, or to the inside of the container 40, and then discharged after bringing the device into the second state. In the example shown in FIG. 15I, the magnetic particles M are moved in the first state to the first portion 11 of the tube 10 by the permanent magnet 70. By doing this, the second plug 32 can be discharged from the tube 10 in a state where the magnetic particles M are not contained in the eluate. The examples shown in FIGS. 15F and 15G show the case where the discharge is performed following the state shown in FIG. 15I. Moreover, when the moving destination of the magnetic particles M is the first portion 11 of the tube 10 or the container 40, it is difficult for the magnetic particles M to pass through the oil of the first plug 31 even removing a magnetic force. Therefore, the second plug 32 can be more easily discharged from the tube 10.

4. Kit

A kit of the embodiment includes the components constituting the main portion of the device described above. Configurations similar to those described above are denoted by the same reference signs and numerals, and the detailed description is omitted.

The kit includes the tube 10 and the plunger 20. Moreover, the kit may include at least one of the container 40, the stopper 50, a lid, an instruction manual, a reagent, and a case. Moreover, in the kit, the tube 10 and the plunger 20 may be included in a state where the plunger 20 is inserted into the tube 10, or in a separate state. Similarly, when the kit includes the container 40, the stopper 50, a lid, and a reagent, they may be included in a separate state, or in appropriate combination with each other. For example, both ends of the tube 10 may be sealed by the stoppers 50. In the case where the both ends of the tube 10 are sealed by the stoppers 50 when the plugs are present in the tube 10 for example, the storage and transfer of the kit become easier. Moreover, both ends of the tubular portion 21 of the plunger 20 may also be sealed, as necessary, by stoppers or the like. Further, in a state where the plunger 20 is inserted into the tube 10 and the first state is established, the end of the second portion 12 of the tube 10 and the end of the tubular portion 21 of the plunger 20 may be each sealed by a stopper or the like.

Further, the opening 41 of the container 40 may be sealed by a lid, a film, or the like, and a reagent or the like may be encapsulated in the container 40. Further, a portion or the whole of components of an adsorption solution may be accommodated in the container 40. Moreover, the container 40 may accommodate an adsorption solution and magnetic particles. By doing this, when a specimen is introduced into the container 40, the step of adsorbing nucleic acids contained in the specimen to the magnetic particles can be performed in the container 40. Due to this, there is no need to prepare another container, so that pretreatment of PCR can be performed further promptly.

The invention is not limited to the embodiments described above, and further various modifications are possible. For example, the invention includes a configuration (for example, a configuration having the same function, method, and result, or a configuration having the same advantage and advantageous effect) that is substantially the same as those described in the embodiments. Moreover, the invention includes a configuration in which a non-essential portion of the configurations described in the embodiments is replaced. Moreover, the invention includes a configuration that provides the same actions and effects as those of the configurations described in the embodiments, or a configuration that can achieve the same advantages. Moreover, the invention includes a configuration in which a publicly known technique is added to the configurations described in the embodiments.

The entire disclosure of Japanese Patent Application No. 2012-128664, filed Jun. 6, 2012 is expressly incorporated by reference herein.

What is claimed is:

1. A device comprising:
   a tube having a first portion and a second portion, the second portion having an inside diameter that is smaller than that of the first portion; and
   a plunger insertable into the tube from a first portion side of the tube, the plunger having:
   a tubular portion configured to fit an inner surface of the first portion; and a rod-like portion extending from the tubular portion, the rod-like portion being configured to fit an inner surface of the second portion, wherein either a first state or a second state is formed when the tubular portion fits the inner surface of the first portion, in the first state, the inner surface of the second portion and the rod-like portion are spaced apart from each other so that the tube forms a communication path fluidly interconnecting an inside of the second portion with an inside of the tubular portion, and in the second state, the inner surface of the second portion and the rod-like portion fit together so as to block the fluid communication path.

2. The device according to claim 1, wherein in the inside of the second portion, a first plug including an oil, a second plug including an eluate not miscible with an oil, and a third plug including an oil are arranged in this order from the first portion side.

3. The device according to claim 1, further comprising a container connectable to the tubular portion, wherein when the container is connected to the tubular portion, the inside of the tubular portion and the inside of the container are communicated with each other.

4. The device according to claim 1, comprising a plurality of the tubes and a plurality of the plungers, wherein the plurality of plungers and the plurality of tubes form, in conjunction with each other, the first state and the second state.

5. The device according to claim 4, further comprising a manifold connectable to the tubular portions of the plurality of plungers, wherein when the manifold is connected to the tubular portions, the insides of the tubular portions and the inside of the manifold are communicated with each other, and the manifold has a plurality of individual passages each connected to the tubular portions, and a common passage connected to the individual passages.

6. The device according to claim 5, wherein the volumes of the individual passages are substantially equal to each other.

7. The device according to claim 5, further comprising a container connectable to the common passage of the manifold, wherein when the container is connected to the manifold, the inside of the manifold and the inside of the container are communicated with each other.

8. The device according to claim 1, wherein the tubular portion has an inner cavity extending therethrough in the longitudinal direction.

9. The device according to claim 1, wherein the rod-like portion is supported by a support so as to form an inner cavity in the tubular portion extending in the longitudinal direction.

10. The device according to claim 1, wherein the tubular portion has a first convex portion, the first convex portion being configured to come into contact with the inner surface of the first portion.

11. The device according to claim 1, wherein the rod-like portion has a second convex portion, the second convex portion being configured to come into contact with the inner surface of the second portion.

* * * * *